(12) United States Patent
Pietrzkowski et al.

(10) Patent No.: US 7,081,449 B2
(45) Date of Patent: Jul. 25, 2006

(54) PYRIDO[2,3-D]PYRIMIDINE AND PYRIMIDO[4,5-D]PYRIMIDINE NUCLEOSIDES

(75) Inventors: Zbigniew Pietrzkowski, San Diego, CA (US); Guangyi Wang, Carlsbad, CA (US); Johnson Lau, Newport Beach, CA (US); Zhi Hong, Aliso Viejo, CA (US); Jean-Luc Girardet, Aliso Viejo, CA (US); Esmir Gunic, Irvine, CA (US)

(73) Assignee: Valeant Research & Development, Costa Mesa, CA (US)

( * ) Notice: Subject to any disclaimer, the term of this patent is extended or adjusted under 35 U.S.C. 154(b) by 461 days.

(21) Appl. No.: 10/221,397

(22) PCT Filed: Jul. 3, 2001

(86) PCT No.: PCT/US01/41242

§ 371 (c)(1),
(2), (4) Date: Dec. 31, 2002

(87) PCT Pub. No.: WO02/03997

PCT Pub. Date: Jan. 17, 2002

(65) Prior Publication Data

US 2003/0144502 A1    Jul. 31, 2003

Related U.S. Application Data

(60) Provisional application No. 60/216,418, filed on Jul. 6, 2000.

(51) Int. Cl.
*A01N 43/04* (2006.01)
*A61K 31/70* (2006.01)

(52) U.S. Cl. .................. 514/45; 514/43; 514/46; 514/47; 514/48; 536/22.1; 536/26.1; 536/26.7

(58) Field of Classification Search .......... 514/43, 514/45, 46, 47, 48; 536/22.1, 26.1, 26.7
See application file for complete search history.

(56) References Cited

U.S. PATENT DOCUMENTS 3,423,398 A    1/1969  Koppaka et al.

OTHER PUBLICATIONS

Wang et al. J. Med. Chem. (2000), vol. 43, pp. 3704-3713.*
*Pyridopyrimidines.7. Ribonucleosides Structurally Related to the Antitumor Antibiotic Sangivamycin*, Gary L. Anderson et al., 1976, et al., J. Org. Chem., vol. 42, No. 6. 1977, pp. 997-1000.
*Pyrido[2,3-d]pyrimidines.III Synthesis of Some 8-(β-D-Ribofuranosyl)pyrido[2,3-d]pyrimidines Structurally Related to the Antibiotic Sangivamycin*[1], Boshra H. Rizkalla et al., J. Org. Chem., vol. 37, No. 25, 1972, pp. 3980-3985.

* cited by examiner

*Primary Examiner*—Patrick Lewis
(74) *Attorney, Agent, or Firm*—Brown Raysman, Millstein Felder & Steiner

(57) ABSTRACT

A purine nucleoside analog includes a pyrido[2,3-d]pyrimidine or a pyrimido[4,5-d]pyrimidine and further has a sugar moiety that is optionally modified at the C2', C3', C4' and/or C5' position. Particularly contemplated compounds also include prodrug forms of the purine nucleoside analogs, and both purine nucleoside analogs and the corresponding prodrugs are employed in the reduction of growth of neoplastic cells.

21 Claims, 8 Drawing Sheets

Effect of contemplated compounds on RNA Pol I and III
As determined by 28S and 18S rRNA production Polymerase II (mRNA)

PYRIDO[2,3-D]PYRIMIDINE AND PYRIMIDO[4,5-D]PYRIMIDINE NUCLEOSIDES

This application claims the benefit of U.S. provisional application No. 60/216,418, filed Jul. 6, 2000, which is incorporated herein by reference in its entirety.

FIELD OF THE INVENTION

The field of the invention is nucleoside analogs.

BACKGROUND OF THE INVENTION

Nucleoside analogs have long been used as antimetabolites for treatment of cancers and viral infections. After entry into the cell, many nucleoside analogs are phosphorylated by nucleoside salvage pathways in a conversion to the corresponding monophosphate by nucleoside kinases, and the monophosphates are subsequently phosphorylated by a kinase to the di-, and triphosphates. Once a nucleoside analog is converted to its triphosphate inside the cell, it can serve as a substrate of DNA or RNA polymerases and can be incorporated into DNA or RNA. Incorporation of certain unnatural nucleoside analogs into nucleic acid replicates or transcripts can interrupt gene expression by early chain termination or loss of function of the modified nucleic acids. In addition, certain nucleoside analogs are very potent inhibitors of DNA and RNA polymerases, which can significantly reduce the rate at which the natural nucleoside can be incorporated.

Moreover, nucleoside analogs can also interfere with a cell in a way other then DNA and/or RNA synthesis. For example, some nucleoside analogs may induce apoptosis of cancer cells, or inhibit certain enzymes other than polymerases. In yet further alternative biological effects, some nucleoside analogs are known to modulate the immune system. Typical examples for biological effects of nucleoside analogs include thymidylate synthase inhibition by 5-fluorouridine, or adenosine deaminase inhibition by 2-chloroadenosine. Further examples include inhibition of S-adenosylhomocysteine hydrolasene by planocin A.

Unfortunately, however, most of the known nucleoside analogs that inhibit tumor growth or viral infections also imply a threat to the normal mammalian cells, primarily because such analogs lack adequate selectivity between normal cells and viral or tumor cells. Therefore, there is still a need to provide methods and compositions for nucleoside analogs with improved specificity and reduced toxicity.

SUMMARY OF THE INVENTION

The present invention provides novel nucleosides having modifications on the nucleoside base and/or the sugar moiety, which may significantly increase selectivity in cytotoxicity to neoplastic cells and/or reduce toxicity of the nucleoside analogs to normal cells. Particularly contemplated nucleosides include a pyrido[2,3-d]pyrimidine, a pyrimido[4,5-d]pyrimidine, and derivatives thereof. The sugar moieties of contemplated compounds may further include modifications on the $C_2$, $C_3$, $C_4$, and/or $C_5$ position.

More specifically, the present invention provides nucleosides having a structure according to formula (I):

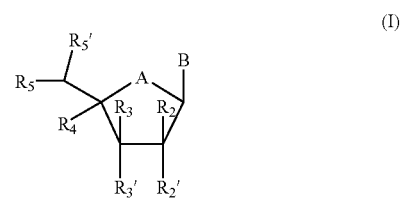

wherein A is O, S, $CH_2$; $R_2$, $R_2'$, $R_3$, and $R_3'$ are independently selected from H, F, OH, $NH_2$, CN, $N_3$, $CONH_2$, and R, where R is lower alkyl, lower alkenyl, lower alkynyl, or lower acyl, and optionally containing at least one of a heteroatom and a functional group; or $R_2$ and $R_2'$ together, or $R_3$ and $R_3'$ together are selected from $=CH_2$, $=CHR''$, $=CR''_2$, $=NR''$, where R'' is H, F, OH, CN, $N_3$, $CONH_2$, lower alkyl, lower alkenyl, lower alkynyl, or lower acyl; $R_4$ and $R_5'$ are independently selected from H, lower alkyl, lower alkenyl, lower alkynyl, or aralkyl, and optionally containing at least one of a heteroatom and a functional group; $R_5$ is H, OH, $OP(O)(OH)_2$, $P(O)(OH)_2$, $OP(O)(OR''')_2$, or $P(O)(OR''')_2$, where R''' is a masking group; and B is selected from the group of heterocyclic radicals consisting of formula (II), (III), (IV) and (V)

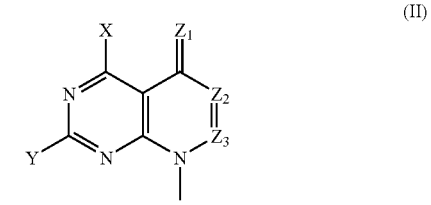

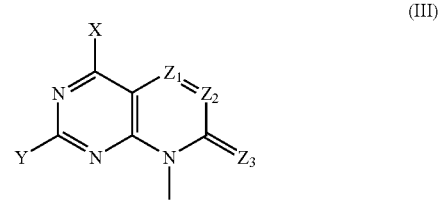

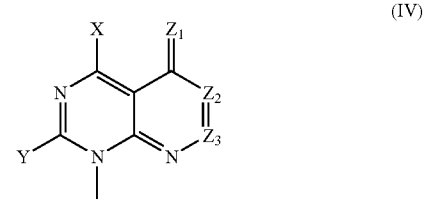

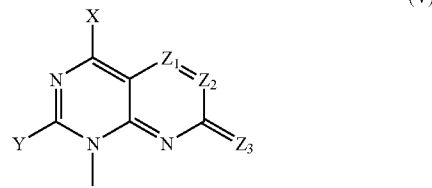

wherein X is H, $NH_2$ or OH; Y is H, $NH_2$, or halogen; $Z_1$ in formula (II) and (IV), and $Z_3$ in formula (III) and (V) is O, S, NR'', CHM, or $CM_2$; $Z_1$ in formula (III) and (V), and $Z_3$ in formula (II) and (IV) is N, CH, or CM; $Z_2$ is N, CH, or CM; where M is F, Cl, Br, OH, SH, NH$_2$, CN, COOR'', C(=NH)NH$_2$, lower alkyl, lower alkenyl, lower alkynyl, aralkyl, or aryl.

In an especially preferred aspect, the nucleoside analog has a structure according to formula (VI):

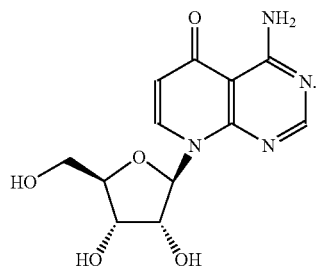

(VI)

In further contemplated aspects of the inventive subject matter, the nucleoside analogs may be modified to form the respective prodrugs, and particularly contemplated modifications include phosphorylation or addition of a phosphonate group at the C$_5$ position of the sugar moiety, modifications on the hydroxyl groups on the sugar moiety, and modifications on the amino group of the nucleobase. It is especially preferred that such modifications can be cleaved from contemplated compounds in a target compartment, target cell, or target organ.

In yet another aspect of the inventive subject matter, a method of inhibiting growth of a neoplastic cell includes a step in which contemplated compounds according to formula (I) are administered to a system, preferably to a mammal, and more preferably to a human. Especially contemplated neoplastic cells include colon cancer cells, breast cancer cells, melanoma cells, glioma cells, and prostate cancer cells. It is further contemplated that the growth inhibition comprises inhibition of RNA polymerase I, RNA polymerase II, and/or RNA polymerase III, and/or induction of apoptosis which may be triggered at least in part by MEK-phosphorylation.

DETAILED DESCRIPTION OF THE INVENTION

Contemplated Compounds

Figure 1:
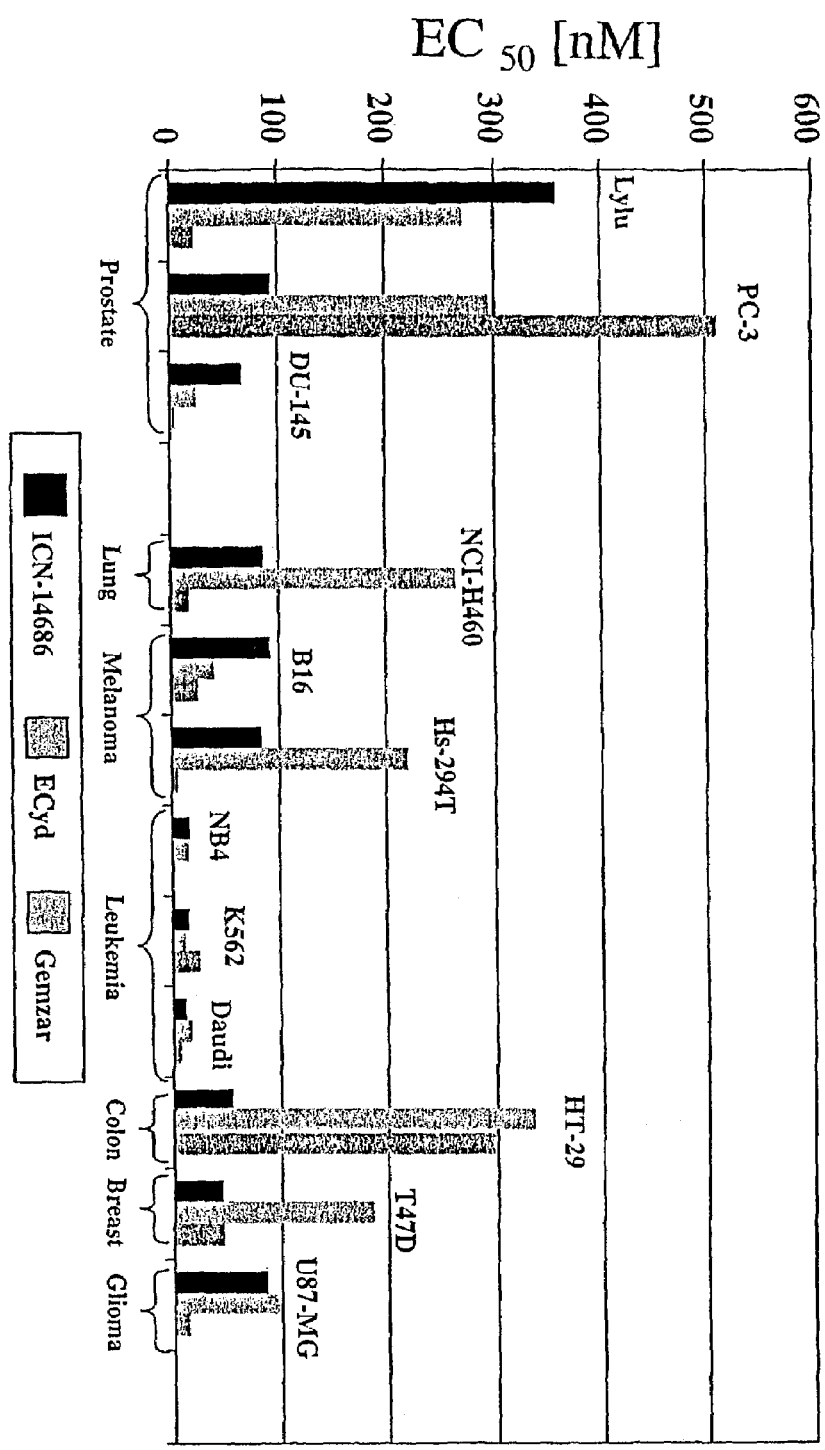
FIG. 1 is a graph depicting comparative cytotoxicity of an exemplary contemplated compound towards various cancer cells.

It is generally contemplated that compounds according to the inventive subject matter have a structure according to formula (I):

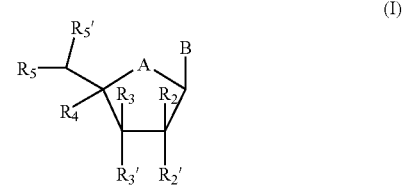

(I)

wherein A is O, S, CH$_2$; R$_2$, R$_2$', R$_3$, and R$_3$' are independently selected from H, F, OH, NH$_2$, CN, N$_3$, CONH$_2$, and R, where R is lower alkyl, lower alkenyl, lower alkynyl, or lower acyl, and optionally containing at least one of a heteroatom and a functional group; or R$_2$ and R$_2$' together, or R$_3$ and R$_3$' together are selected from =CH$_2$, =CHR'', =CR''$_2$, =NR'', where R'' is H, F, OH, CN, N$_3$, CONH$_2$, lower alkyl, lower alkenyl, lower alkynyl, or lower acyl; R$_4$ and R$_5$' are independently selected from H, lower alkyl, lower alkenyl, lower alkynyl, or aralkyl, and optionally containing at least one of a heteroatom and a functional group; R$_5$ is H, OH, OP(O)(OH)$_2$, P(O)(OH)$_2$, OP(O)(OR''')$_2$, or P(O)(OR''')$_2$, where R''' is a masking group; and B is selected from the group of heterocyclic radicals consisting of formula (II), (III), (IV), and (V)

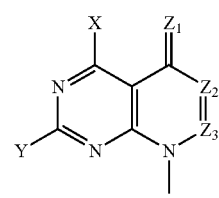

(II)

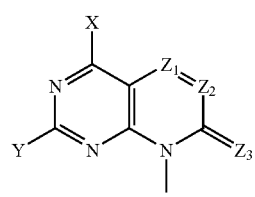

(III)

-continued

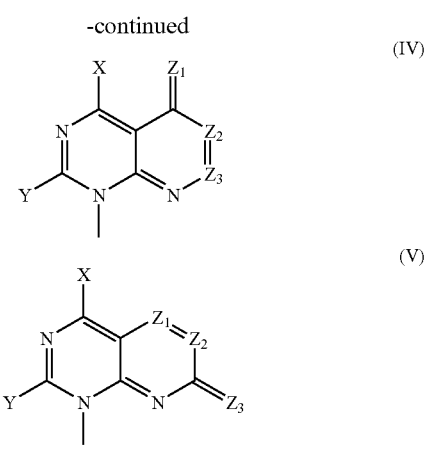

wherein X is H, $NH_2$ or OH; Y is H, $NH_2$, or halogen; $Z_1$ in formula (II) and (IV), and $Z_3$ in formula (III) and (V) is O, S, NR", CHM, or $CM_2$; $Z_1$ in formula (III) and (V), and $Z_3$ in formula (II) and (IV) is N, CH, or CM; $Z_2$ is N, CH, or CM; where M is F, Cl, Br, OH, SH, $NH_2$, CN, COOR", C(=NH)$NH_2$, lower alkyl, lower alkenyl, lower alkynyl, aralkyl, or aryl.

In a preferred aspect of the inventive subject matter, contemplated compounds have a heterocyclic radical according to formula (II), A is oxygen in the sugar moiety of the nucleoside analog, and it is even more preferred that in such nucleoside analogs X is $NH_2$, $Z_1$ is O, and $Z_2$ and $Z_3$ are CH. While not limiting the inventive subject matter, it is still further preferred that $R_4$ and $R_5'$ are hydrogen, and $R_5$ is OH in the sugar moiety.

In further particularly preferred aspects of the inventive subject matter, contemplated nucleoside analogs have a structure according to formula (VI):

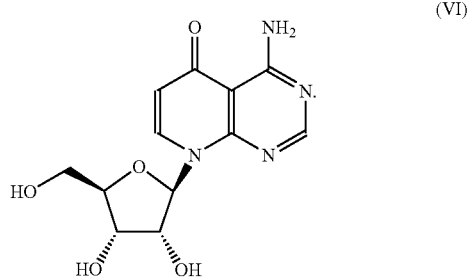

With respect to the stereochemical configuration of contemplated compounds, it should be appreciated that the sugar need not be restricted to the D-configuration, but may also be in the L-configuration. Similarly, it is contemplated that suitable molecules may include one or more chiral centers, which may be enantiomeric pure (i.e., in R-, or S-configuration) or in a racemic mixture (i e., in R- and S-configuration). Likewise, where substituents (e.g., base or OH groups) may exhibit an orientation in the α- or β-position, both positions are contemplated.

Furthermore, it should be appreciated that contemplated compounds may be modified to their corresponding prodrug. The term "prodrug" as used herein refers to any modification of contemplated compounds that (a) changes the molecular weight of contemplated compounds and/or (b) alters the bioavailability of contemplated compounds with respect to a target cell and a non-target cell. For example, a prodrug may be prepared by esterification of a hydroxyl group of contemplated compounds with an organic acid (thereby changing the molecular weight, but not necessarily changing the bioavailability to a target cell). On the other hand, contemplated compounds may be converted to a prodrug to include a cyclic phosphonate ester (thereby increasing bioavailability to hepatic cells).

Moreover, it should be especially appreciated that prodrug forms of contemplated compounds may be entirely or partially re-converted to the contemplated compounds in a target organ, target cell, or target compartment (or in any non-target environment). Reconversion may include various mechanisms and especially contemplated mechanisms are enzymatic conversion, oxidation and/or reduction.

Prodrugs may also be employed to increase the specificity of contemplated compounds with respect to a target organ, target cell, or target compartment. For example, contemplated compounds my be coupled to cholesterol (or a cholesterol derivative) to increase the concentration of contemplated compounds within the hepato-biliary circulation. Alternatively, contemplated compounds may be coupled to a compound that has a corresponding receptor on a target cell, thereby increasing the concentration of contemplated compounds at or in the target cell. In a yet another example, contemplated compounds may be coupled to a nuclear translocation signal to increase the concentration of contemplated compounds within the nucleus of a cell.

Furthermore, prodrugs may be employed to reduce accumulation of contemplated compounds in non-target organs, non-target cells, or non-target compartments. For example, contemplated compounds may be modified such that a non-target cell will have a significantly reduced rate of uptake of contemplated compounds when such compounds are modified to a prodrug. Thus, and especially where contemplated compounds exhibit cytotoxicity to a non-target cell, prodrugs may be employed to reduce cytotoxicity of contemplated compounds in cells or organs other than the target cells or target organs.

In yet further contemplated aspects of the inventive subject matter, suitable compounds may be covalently coupled to pharmacologically active or inactive moieties. For example, pharmacologically active moieties include antineoplastic drugs such as anti-metabolites (e.g., Pentostatin™), DNA polymerase inhibitors (e.g., Gemzar™), RNA polymerase inhibitors (e.g, ECyd™), platinum derivatives (e.g., Paraplatin™), anti-estrogens (e.g., Nolvadex™), Taxanes (e.g., Taxotere™), GnRH analogs (e.g., Lupron™), DNA polymerase inhibitors (e.g., Gemzar™), topoisomerase inhibitors (e.g., Hycamptin™), biphosphonates (e.g., Aredia™), somatostatins (e.g., Sandostatin™), interferons (e.g., IntronA™), nucleoside analogs (e.g., Ribavirin™), and IMPDH-inhibitors (e.g., Tiazofurin™).

Pharmacologically inactive moieties include biological and non-biological moieties. For example, where target specificity is particularly desirable, contemplated compounds may be coupled to an antibody, an antibody fragment, or a synthetic antibody (e.g, scFv). In a further example, contemplated compounds may be coupled to a chelator (e.g., that binds a radionucleid). Alternatively, where prolongation of serum half-life or reduced immunogenicity is particularly preferred, contemplated compounds may be coupled to inert or biodegradable polymers (e.g., dextran, polyethylene glycol, etc.).

With respect to the mode of coupling contemplated compounds to other moieties, all known methods of coupling are considered appropriate and especially include covalent coupling (with or without a separate linker molecule), hydrogen bonding, and hydrophobic/hydrophilic interactions.

In still further aspects of the inventive subject matter, contemplated compounds may also be in the form of their respective salts, wherein the salt may be a salt of an organic or inorganic acid or base (e.g., actetate or morpholino salt, HCl salt). There are numerous pharmacologically acceptable salts known in the art, and all of the known salts are considered suitable for use in conjunction with the teachings presented herein.

Synthesis of Contemplated Compounds

Synthesis of Modified Ribofuranoses

The exemplary schemes below show the synthetic routes to some of the contemplated compounds. Compound 1, prepared according to a published procedure (Jones et al. Methods in Carbohydrate Chemistry (edited by Whistler and Moffat), vol. VI, pp315–322, Academic Press, New York, (1972)), was treated with a variety of nucleophiles such as Grignard reagents to give 2, which was benzoylated or acetylated and subsequently treated with trifluoroacetic acid to give compound 4. Benzoylation and the subsequent treatment with acetic anhydride/acetic acid in the presence of sulfuric acid gave compound 6, which was used for condensation with pyrido[2,3-d]pyrimidine or pyrimido[4,5-d]pyrimidine bases.

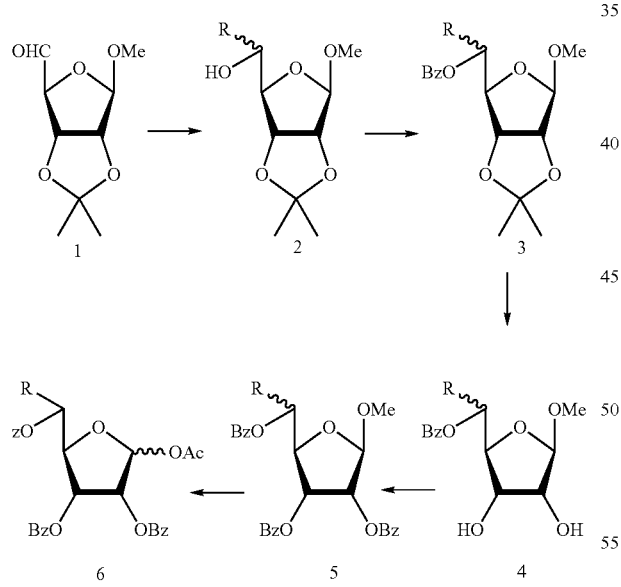

6a R = Me  6b R = ethynyl  6c R = vinyl  6d R = allyl

Compound 2a (5(R)-C-methyl derivative) was converted to the sulfonate 7, which was subjected to nucleophilic substitution to give the configurationally inverted compound 8. Deprotection of the isopropylidene and the subsequent acetylation gave the tetraacetate 9.

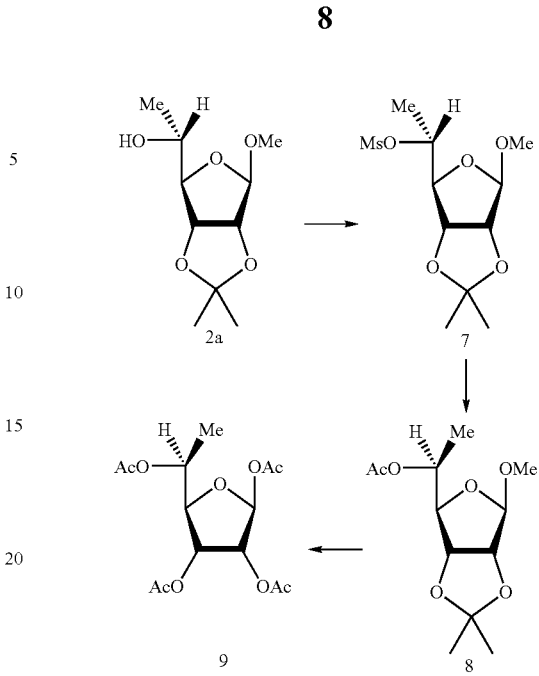

Compound 1 was treated with formaldehyde in aqueous sodium hydroxide to give 4'-hydroxymethyl derivative 10, which was selectively protected to afford compound 11.

The subsequent protection with DMT and removal of TBS gave compound 13, which can be converted to a variety of substituents. The 4-C-substituted derivatives subjected to the similar transformations as 5-C-substituted ribofuranoses can be converted to compound 17, which is used for condensation with nucleoside bases.

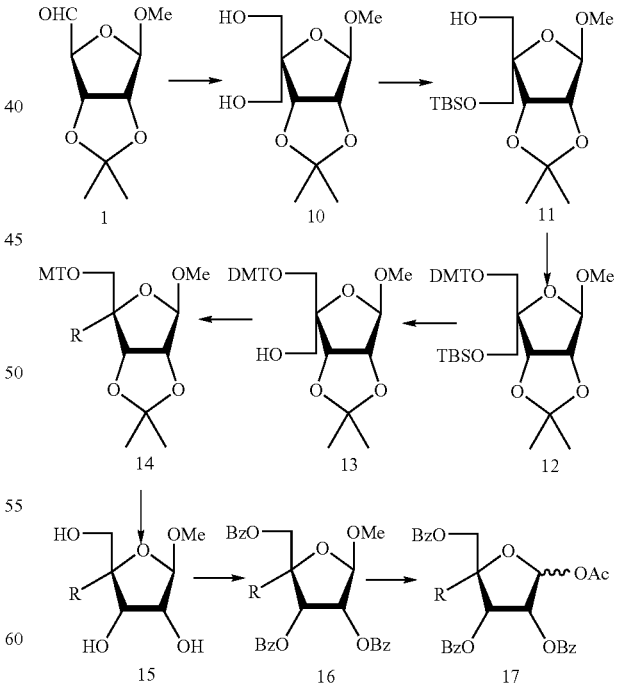

a R = methyl  b R = vinyl  c R = ethyl  d R = HOCH$_2$

Compound 13 was converted to 18, which was subjected to Wittig reaction to give 19. Hydrogenation of 19 over palladium afforded 20. Compound 13 was converted to the 4-C-phenoxythiocarbonyloxymethyl derivative 21, which was reacted with tris(trimethylsilyl)silane (9.0 mL, 29 mmol) and then with 1,1'-azobis(cyclohexanecarbonitrile) to give 22.

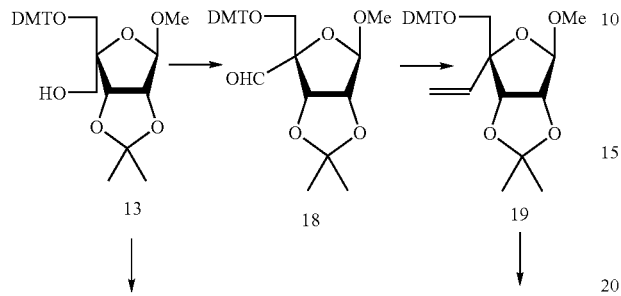

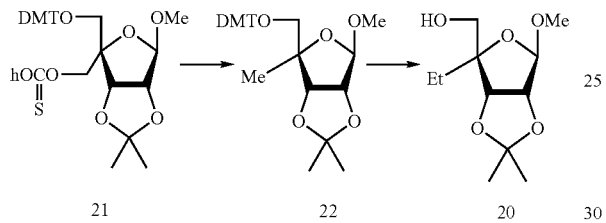

Where contemplated compounds include a sugar moiety that is not modified at the $C_4'$ or $C_5'$ position (e.g., L-ribofuranose, 2'-hydroxy-2'-ethynyl-L-ribofuranose), condensation of the corresponding protected sugar moiety (in D- or L-configuration) is carried out following procedures well known in the art.

Synthesis of Modified Pyridopyrimidine Nucleosides

The 5'-substituted nucleoside analogs are prepared from the condensation of the silylated pyrido[2,3-d]pyrimidine bases and the properly protected, modified ribofuranoses. The following scheme shows synthesis of 4-amino-5-oxo-pyrido[2,3-d]pyrimidine 25. Compound 23, prepared according to a reported procedure (Archive der Pharmazie 1985, 318, 481–486), was refluxed with chlorotrimethylsilane and sodium iodide in acetonitrile to give 24. Reaction of 24 with formamidine acetate under reflux afforded compound 25.

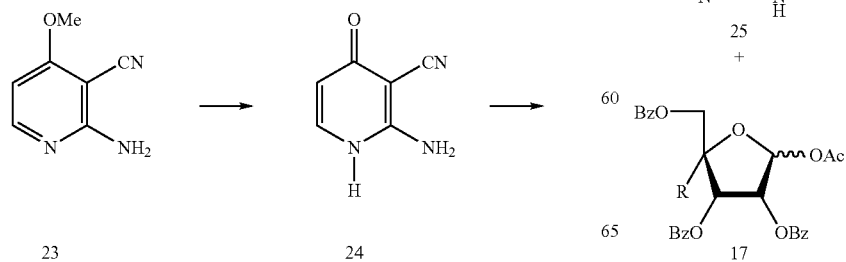

-continued

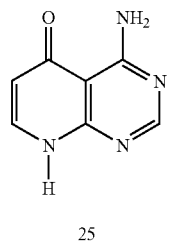

The following schemes show the condensation of the pyrido[2,3-d]pyrimidine 25 and the modified ribofuranoses 6 and 17. Compound 25 was treated with (bis(trimethylsily)acetamide to give the silylated pyridopyrimidine, which was reacted with 6 or 17 to give 26 or 28. Removal of benzoyl afforded the pyrido[2,3-d]pyrimidine nucleosides 27 and 29, respectively.

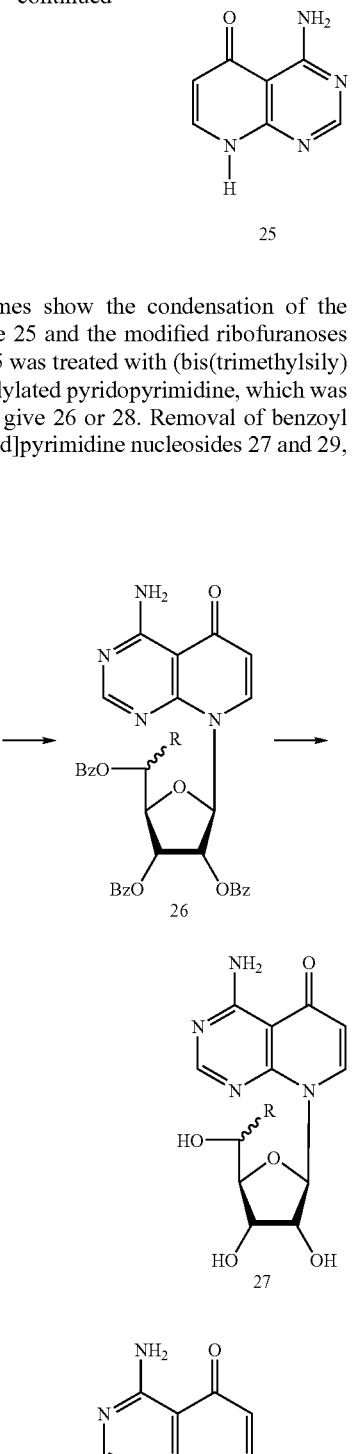

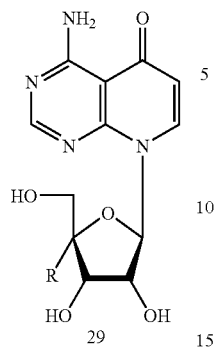

29

R = Me, ethyl, vinyl, propyl, allyl, hydroxymethyl

Other sugar-modified pyridopyrimidine or pyrimidopyrimidine nucleosides can be prepared either through condensation of nucleoside bases and modified sugars or through modifications of the nucleosides. For example, 4-amino-5-oxo-pyrido[2,3-d]pyrimidine riboside (27 or 29 R=H) was converted to 2'-deoxy derivative 30 by a similar procedure described for 2'-deoxyadenosine, and 4-amino-5-oxo-pyrido[2,3-d]pyrimidine xyloside 34 was prepared by condensation.

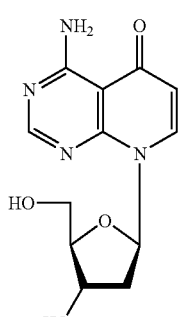

30

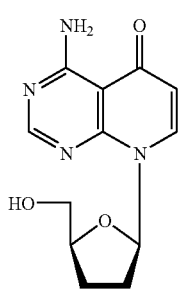

31

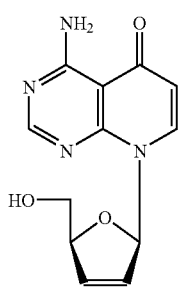

32

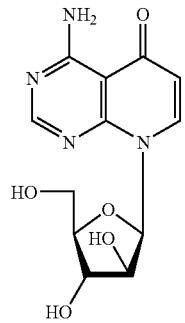

33

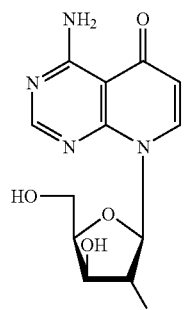

34

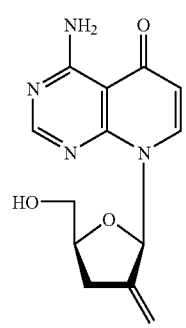

35

4-Amino-5-oxopyrido[2,3-d]pyrimidine was condensed with a variety of 1-O-acetylated pentose sugars via Vorbrüggen reactions. Further derivatizations of the nucleosides provided an additional group of pyrido[2,3-d]pyrimidine nucleosides.

Synthesis of Modified Pyrimidopyrimidine Nucleosides

The 5'-substituted nucleoside analogs are prepared from the condensation of the silylated pyrimido[4,5-d]pyrimidine bases and the properly protected, modified ribofuranoses. The synthesis of pyrimido[4,5-d]pyrimidine nucleosides follows a protocol substantially similar to the synthetic procedure as outlined above.

Depending on the reaction conditions of the condensation reactions employed to couple the sugar moiety to the pyrido[2,3-d]pyrimidine or pyrimido[4,5-d]pyrimidine base, the corresponding nucleoside analogs may be connected at the $N_1$ or $N_8$ atom of the base. In any case, the glycoslyation site of the base was established by X-ray crystal structure.

Uses of Contemplated Compounds

It should generally be recognized that the contemplated compounds may be employed in any treatment or therapy of a system that positively responds to administration of contemplated compounds. However, it is particularly preferred that the contemplated compounds may be employed in antineoplastic treatments and antiviral treatments (as a direct antiviral compound and/or as an indirect antiviral compound), and in treatments to modulate the immune system.

Antineoplastic Treatments

It is generally contemplated that compounds according to the inventive subject matter may be employed as antineoplastic agents that directly or indirectly inhibit growth, invasiveness, and/or spread of a neoplastic cell or cell population. It is particularly contemplated that a method of treating a neoplastic disease in a patient comprises a step in which the contemplated compounds are administered to the patient at a dosage effective to inhibit growth of a neoplastic cell, and an especially preferred compound is the compound according to formula (VI, supra). Contemplated dosages are in the range between 0.01–100 mg/kg, and more preferably between 5–50 mg/kg. However, alternative dosages, routes, schedules and formulations are also contemplated, and suitable alternative administrations are described below. While the use of contemplated compounds is not restricted to a particular neoplastic cell or neoplastic disease, especially contemplated neoplastic cells include colon cancer cells, breast cancer cells, melanoma cells, glioma cells, and prostate cancer cells.

Antiviral Treatments

It is generally contemplated that compounds according to the inventive subject matter may be employed as a direct and/or indirect antiviral agent in a viral infection. It is particularly contemplated that a method of treating a viral infection in a patient comprises a step in which the contemplated compounds are administered to the patient at a dosage effective to inhibit viral propagation (i.e., a process involving a host cell in which one or more than one virus causes the host cell to produce one or more copies of the virus, wherein the term "to produce" refers to nucleotide synthesis, protein processing, and protein assembly), and wherein the composition comprises at least one of the contemplated compounds. Contemplated dosages are in the range of between 0.1–100 mg/kg, and more preferably between 5–50 mg/kg. However, alternative dosages, routes, schedules and formulations are also contemplated, and suitable alternative administrations are described below. While the use of contemplated compounds is not restricted to a particular virus in a particular viral infection, especially contemplated viral infections are an HIV infection, an HCV infection, an HBV infection, an RSV infection, an influenza virus infection, and a parainfluenza virus infection.

Immunomodulation

It is generally contemplated that compounds according to the inventive subject matter may be employed as immunomodulatory compounds, and it is particularly contemplated that such compounds may be employed to modulate the balance between a Type 1 response and a Type 2 response of an immunocompetent cell (e.g., T-cell) towards a challenge. More specifically, it is contemplated that the compounds according to the inventive subject matter may increase the Type 1 response relative to a Type 2 response (either by increasing the Type 1 response or by decreasing the Type 2 response), however, it is also contemplated that the compounds of the inventive subject matter may increase the Type 2 response relative to a Type 1 response (either by increasing the Type 2 response or by decreasing the Type 1 response). In still farther contemplated uses of the compounds according to the inventive subject matter, it should be appreciated that contemplated compounds may also be employed as immunosuppressive agents at a concentration effective to suppress both Type 1 and Type 2 responses.

Administration of Contemplated Compounds

With respect to administration of contemplated compounds, it should be appreciated that the compounds may be administered under any appropriate protocol in any appropriate pharmaceutical formulation. It is generally preferred, however, that contemplated compounds are orally administered. In further aspects of the inventive subject matter, it should be appreciated that various alternative administrations are also suitable, and it should still further be recognized that a particular administration will generally depend on chemical stability, bioavailability, dosage, formulation, and/or desired pharmacokinetic/pharmacodynamic properties of contemplated compounds. Thus, appropriate administrations will include oral administration (e.g., tablet, syrup, etc.), topical delivery (e.g., ointment, spray, cream, etc.), parenteral systemic delivery (e.g., inhalation), and direct or indirect delivery to the blood stream (e.g., i.v. or i.m. injection, etc.).

Consequently, the formulation of contemplated compounds may vary considerably. For example, where the drug or drug composition exhibits sufficient stability to pass through the gastro-intestinal system without undesired chemical or enzymatic modification, oral formulations may include syrup, tablets, gel caps, powder, etc. On the other hand, where absorption or passage of contemplated compounds through the gastrointestinal tract into the blood stream is problematic, suitable formulations especially include injectable solutions or suspensions (e.g., physiological saline solution buffered to a pH of about 7.2 to 7.5).

With respect to the dosage of contemplated compounds, it should be appreciated that various dosages are suitable, and contemplated dosages typically are in the range of 0.1 mg/kg to several 100 mg/kg, and even more. For example, where contemplated compounds are excreted or metabolized at a relatively low rate, or where long-term treatment is desired, dosages will typically be in the range between 0.5 mg–10 mg/kg. On the other hand, where bioavailability of contemplated drugs is relatively low, or where metabolic conversion is relatively fast, dosages will typically be in the range between 10 mg/kg–100 mg/kg.

With respect to the dosage of contemplated compounds, it should further be appreciated that at least some of the compounds according to the inventive subject matter may be phosphorylated in vivo. Consequently, and especially where immediate bioavailability is desired, dosages may be reduced where contemplated compounds are administered in a phosphorylated form.

The schedule of administration may vary considerably, and contemplated schedules include a single dose over the entire course of treatment, multiple single daily doses over the entire course of treatment, multiple daily doses, and permanent dosing (e.g., permanent infusion, implanted osmotic pump, etc.) for at least part of the course of treatment. While it is generally preferred that suitable schedules sustain constant delivery of contemplated compounds, burst delivery (i.e., at least one administration at a first dose followed by at least one more administration at a dose lower than the first dose) is also appropriate. With respect to the duration of treatment, it is contemplated that appropriate durations may vary between a single administration and several days, several weeks, several years, and even longer. For example, where contemplated compounds are employed in a cell culture, a single administration, or relatively short administration may be sufficient. On the other hand, where contemplated compounds are administered to treat an acute phase of a disease, appropriate treatment duration may be in the range between several days and several weeks. Similarly, where chronic diseases are treated by administration of contemplated compounds, extended administration over one or more years may be suitable.

In still further alternative aspects of the inventive subject matter, contemplated compounds may be combined with additional pharmaceutically active substances to assist in the treatment of various diseases, and particularly neoplastic diseases. Additional pharmaceutically active substances may be administered separately or together, and when administered separately, administration may occur simultaneously or separately in any order. Especially contemplated additional pharmaceutically active substances include drugs commonly used as chemotherapy for treatment of cancer and immune modulator substances. For example, chemotherapeutic agents include anti-metabolites (e.g., Pentostatin™), DNA polymerase inhibitors (e.g, Gemzar™), RNA polymerase inhibitors (e.g., ECyd™), platinum derivatives (e.g., Paraplatin™), anti-estrogens (e.g., Nolvadex™), Taxanes (e.g., Taxotere™), GnRH analogs (e.g., Lupron™), DNA polymerase inhibitors (e.g., Gemzar™), topoisomerase inhibitors (e.g., Hycamptin™), biphosphonates (e.g., Aredia™), somatostatins (e.g., Sandostatin™), nucleoside analogs (e.g., Ribavirin™), and IMPDH-inhibitors (e.g., Tiazofurin™). Contemplated immunomodulatory substances include cytokines (e.g., interferon α and γ, IL2, IL4, IL6, IL8, IL10, and IL12), cytokinins (e.g., kinetin), and chemokines (e.g., MIP-1).

EXAMPLES

The following examples provide exemplary synthesis, in vitro/in vivo experiment, and are intended to illustrate but not to limit the invention.

Synthesis

Preparation of 2,3-O-isopropylidene-5(R,S)-C-ethynyl-1-O-methyl-β-D-ribofuranose To a stirred solution of methyl 4-C,5-O-didehydro-2,3-O-isopropylidene-β-D-ribofuranoside (Jones et al. *Methods in Carbohydrate Chemistry* Vol 1, pp 315–322 (1972), 4.00 g, 19.78 mmol) in anhydrous THF (20 mL) at −42° C. under argon was added dropwise ethynylmagnesium bromide (0.5 M in THF, 80 mL, 40 mmol). Upon addition, the resulting mixture was slowly warmed up to 0° C. (~90 min.). The reaction was quenched by adding ice (50 g)/water (50 mL) and the mixture was stirred for 30 min. After neutralization with 10% aq. acetic acid, the mixture was extracted with ethyl acetate twice. The combined organic layer was dried (Na$_2$SO$_4$) and concentrated. Chromatography on silica (ethyl acetate-hexanes 1:4) gave 3.48 g of the titled compound (R/S ratio 1:1) as a white solid. Similarly, the following compounds were prepared: 1-O,5(R)-C-Dimethyl-2,3-O-isopropylidene-β-D-ribofuranose from 4-C,5-O-didehydro-2,3-O-isopropylidene-1-O-methyl-β-D-ribofuranose and methylmagnesium bromide; 2,3-O-Isopropylidene-1-O-methyl-5(R)-C-vinyl-β-D-ribofuranose from 4-C,5-O-didehydro-2,3-O-isopropylidene-1-O-methyl-β-D-ribofuranose and vinylmagnesium bromide; 5(R)-C-Allyl-2,3-O-isopropylidene-1-O-methyl-β-D-ribofuranose from 4-C,5-O-didehydro-2,3-O-isopropylidene-1-O-methyl-β-D-ribofuranose and allylmagnesium bromide.

Preparation of 5-O-acetyl-1-O,5(S)-C-dimethyl-2,3-O-isopropylidene-β-D ribofuranose To a stirred solution of 1-O,5(R)-C-dimethyl-2,3-O-isopropylidene-β-D-ribofuranose (7.24 g, 33.17 mmol) in anhydrous pyridine (50 mL) at 0° C. was added methanesulfonyl chloride (3.1 mL, 39.92 mmol). The resulting mixture was stirred at room temperature for 1 h, cooled to 0° C., quenched by adding water (1.0 mL), and stirred at room temperature for 30 min. The solvent was evaporated and the residue was dissolved in ethyl acetate, washed with brine three times, dried (Na$_2$SO$_4$) and concentrated. Chromatography on silica (30% EtOAc in hexanes) gave 8.62 g of the methylate as a colorless syrup.

A stirred suspension of 1-O,5(R)-C-dimethyl-2,3-O-isopropylidene-5-O-methanesulfonyl-β-D-ribofuranose (8.62 g, 29.1 mmol) and NaOAc (anhydrous, 3.5 g, 42.5 mmol) in anhydrous DMF (350 mL) was heated at 125° C. under argon for 4 days. The solvent was evaporated and the residue chromatographed on silica (25% EtOAc in hexanes) to give 4.0 g of the titled compound as a white solid.

Preparation of 5-deoxy-2,3-O-isopropylidene-1-O-methyl-β-D-ribofuranose

To a stirred solution of 2,3-O-isopropylidene-1-O-methyl-β-D-ribofuranose (14.2 g, 70.0 mmol) in anhydrous pyridine (250 mL) at 10° C. was added in portions (over 30 min) p-toluenesulfonyl chloride (19.1 g, 100 mmol). The resulting mixture was stirred at room temperature for 18 h, cooled to 0° C., quenched by adding water (5.0 mL), and stirred at room temperature for 30 min. The solvent was evaporated. The residue was dissolved in ethyl acetate, washed with brine three times, dried (Na$_2$SO$_4$) and concentrated to dryness. Chromatography on silica (ethyl acetate-hexanes 1:3) gave 24.1 g of the tosylate as a white solid.

To a stirred suspension of LiAlH$_4$ (4.58 g, 120.5 mmol) in anhydrous diethyl ether (120 mL) was added the tosylate (13.1 g, 36.55 mmol) in diethyl ether-toluene (2.5:1, 140 mL). The resulting mixture was refluxed for 22 h, cooled to room temperature, diluted with ethyl acetate (25 mL) quenched by adding water (5.0 mL). The solvent was evaporated. The residue was dissolved in ethyl acetate, washed with brine three times, dried (Na$_2$SO$_4$) and concentrated to dryness. Chromatography on silica (ethyl acetate-hexanes 1:3) gave 3.58 g of the titled compound as a colorless liquid.

Preparation of 5(R)-C-allyl-5-O-benzoyl-1-O-methyl-β-D-ribofuranose

To a stirred solution of 5(R)-C-allyl-2,3-O-isoproplidene-1-O-methyl-β-D-ribofuranose (4.49 g, 18.38 mmol) in anhydrous pyridine (40 mL) at 0° C. was added benzoyl chloride (2.7 mL, 23.0 mmol). The resulting mixture was stirred at room temperature for 18 h, cooled with ice, quenched by adding water (1 mL), and stirred at room temperature for 30 min. The solvent was evaporated and the residue was dissolved in ethyl acetate, washed with brine three times, dried (Na$_2$SO$_4$) and concentrated. Chromatography on silica (12% ethyl acetate in hexanes) gave 6.26 g of 5(R)-C-allyl-5-O-benzoyl-2,3-O-isopropylidene-1-O-methyl-β-D-ribofuranose as a colorless syrup.

A solution of 5(R)-C-allyl-5-O-benzoyl-2,3-O-isopropylidene-1-O-methyl-β-D-ribofuranose (6.2 g, 17.8 mmol) in TFA-H$_2$O mixture (9:1) was stirred at 0° C. for 90 min and concentrated to dryness at 0° C. The residue was dissolved in methanol-toluene mixture (20 mL, 1:1) and concentrated to dryness. Chromatography on silica (ethyl acetate-hexanes 1:1) gave 3.70 g of the titled compound as a white solid. Similarly, the following compounds were prepared: 5-O-Benzoyl-5(R,S)-C-ethynyl-1-O-methyl-β-D-ribofuanose (R/S ratio: 1:1) from 5-O-benzoyl-5(R,S)-C-ethynyl-2,3-O-isopropylidene-1-O-methyl-β-D-ribofuranose; 5-O-Benzoyl-4-C-benzoyloxymethyl-1-O-methyl-β-D-ribofuranose from 5-O-benzoyl-4-C-benzoyloxymethyl-2,3-O-isopropylidene1-O-methyl-β-D-ribofuranose; 5-O-Benzoyl-1-O-methyl-5(R)-C-vinyl-β-D-ribofuranose from 2,3-O-isopropylidene-1-O-methyl-5(R)-C-vinyl-β-D-ribofuranose.

Preparation of 1-O-acetyl-5(R)-C-allyl-2,3,5-tri-O-benzoyl-D-ribofuranose

To a stirred solution of 5(R)-C-allyl-5-O-benzoyl-1-O-methyl-62-D-ribofuranose (3.60 mg, 11.68 mmol) in anhydrous pyridine (80 mL) at 0° C. was added benzoyl chloride (3.0 mL, 25.84 mmol). The resulting mixture was stirred at room temperature for 18 h, cooled with ice, quenched by adding water (1 mL), then stirred at room temperature for 30 min. The mixture was concentrated, diluted with ethyl acetate, washed with brine three times, dried ($Na_2SO_4$) and concentrated to dryness. Chromatography on silica (15% ethyl acetate in hexanes) gave 5.3 g of the titled compound as a colorless syrup.

To a stirred solution of 5(R)-C-allyl-2,3,5-tri-O-benzolyl-1-O-methyl-β-D-ribofuranose (4.0 g, 7.74 mmol) in acetic acid (14 mL) and acetic anhydride (1.75 mL, 18.36 mmol) at 0° C. was added concentrated sulfuric acid (200 μL, 3.79 mmol in 4.0 mL of acetic acid). The resulting mixture was stirred at room temperature for 20 h, cooled to 0° C., diluted with cold ethyl acetate, washed with water, dilute $NaHCO_3$ and then brine, dried ($Na_2SO_4$), and concentrated. Chromatography on silica (ethyl acetate-hexanes 1:4) gave 2.82 g of the titled compound (α/β ratio: 1:2) as a colorless foam. Similarly, the following compounds were prepared: 1-O-Acetyl-5(R,S)-C-ethynyl-2,3,5-tri-O-benzolyl-β-D-ribofuranose (R/S ratio: 1:1 and α/β ratio: 1:2) from methyl 5(R,S)-C-ethynyl-2,3,5-tri-O-benzolyl-β-D-ribofuranoside; 1-O-Acetyl-4-C-benzoyloxymethyl-2,3,5-tri-O-benzoyl-D-ribofuranose (α/β ratio: 1:3) from methyl 4-C-benzoyloxymethyl-2,3,5-tri-O-benzoyl-β-D-ribofuranoside; 5(R)-C-Methyl-1,2,3,5-tetra-O-acetyl-β-D-ribofuranose from 1-O,5(R)-C-dimethyl-2,3-O-isopropylidene-β-D-ribofuranose; 5(S)-C-Methyl-1,2,3,5-tetra-O-acetyl-β-D-ribofuranose from 5-O-acetyl-1-O,5(R)-C-dimethyl-2,3-O-isopropylidene-β-D-ribofuranose; 5-Deoxy-1,2,3-tri-O-acetyl-β-D-ribofuranose from 5-O-acetyl-2,3-O-isopropylidene1-O-methyl-β-D-ribofuranose; 1-O-Acetyl-2,3,5-tri-O-benzoyl-5(R)-C-vinyl-β-D-ribofuranose from 1-O-methyl-2,3,5-tri-O-benzoyl-5(R)-C-vinyl-β-D-ribofuranose.

Preparation of 1-O-methyl-5-O-benzoyl-4-C-benzoyloxymethyl-β-D-ribofuranose

To a stirred solution of 4-C,5-O-didehydro-2,3-O-isopropylidene-1-O-methyl-β-D-ribofuranose 1 (20.22 g, 100 mmol) in dioxane (380 mL) at 0° C. was added dropwise formaldehyde (37% solution, 76 mL) and then 2 M NaOH (188 mL). The resulting reaction mixture was stirred at room temperature for 20 h, cooled to 0° C., neutralized (10% acetic acid), concentrated (~50%), and extracted with methylene chloride twice. The combined organic layer was dried over $Na_2SO_4$ and concentrated to dryness. Chromatography on silica (4% methanol in chloroform) gave 20.2 g of 1-O-methyl-5-O-benzoyl-2,3-O-isopropylidene-4-C-benzoyloxymethyl-β-D-ribofuranose as a white solid.

A solution of 1-O-methyl-5-O-benzoyl-2,3-O-isopropylidene-4-C-benzoyloxy-methyl-β-D-ribofuranose (2.0 g, 4.5 mmoles) in a 9:1 (v/v) mixture of trifluoroacetic acid and water (11 mL) was stirred at 0° C. for 2 h and evaporated to dryness. The residue was dissolved in methanol and evaporated (3 times), then dissolved in pyridine and evaporated. The residue was subjected to silica gel chromatography [methanol (0–0.5%) in dichloromethane] to give 1.7 g of the titled compound as an oil.

Preparation of 1-O-acetyl-2,3,5-tri-O-benzoyl-4-C-benzoyloxymethyl-β-D-ribofuranose To a solution of 1-O-methyl-5-O-benzoyl-4-C-benzoyloxymethyl-β-D-ribofuranose (1.7 g, 4.2 mmoles) in pyridine (14 mL) was added benzoyl chloride (1.2 mL, 10 mmoles). The reaction mixture was stirred at 25° C. for 16 h and methanol (5 mL) was added. The solvents were evaporated and the residue was dissolved with ethyl acetate (20 mL) and water (10 mL). The organic layer was dried over sodium sulfate, filtered, and the filtrate was evaporated to dryness. The residue was subjected to silica gel chromatography [methanol (0–0.5%) in dichloromethane] to give 2.4 g of Preparation of 1-O-methyl-2,3,5-tri-O-benzoyl-4-C-benzoyloxymethyl-β-D-ribofuranose as a white solid.

Sulfuric acid (97%, 75 mL) was added to a solution of 1-O-methyl-2,3,5-tri-O-benzoyl-4-C-(benzoyloxymethyl)-β-D-ribofuranose (1.7 g, 2.8 mmoles) in a mixture of acetic acid (6.7 mL) and acetic anhydride (0.67 mL) at 0° C. The reaction mixture was stirred at 25° C. for 15 h and diluted with ethyl acetate (50 mL) and water (10 mL). This solution was washed with brine (3 times), with a saturated aqueous solution of sodium bicarbonate, dried over sodium sulfate, filtered, and the filtrate was evaporated to dryness. The residue was subjected to silica gel chromatography [ethanol (0–2%) in dichloromethane] to give 1.4 g of the titled compound as a white solid.

Preparation of 4-C-(4,4'-dimethoxytrityloxymethyl)-2,3-O-isopropylidene-1-O-methyl-β-D-ribofuranose A solution of 4,4'-dimethoxytrityl chloride (6.0 g, 18 mmol) in pyridine (18 mL) was added to a solution of 4-C-hydroxymethyl-2,3-O-isopropylidene-1-O-methyl-β-D-ribofuranose (3.5 g, 15 mmol) in pyridine (60 mL) stirred at 0° C. The reaction mixture was stirred at room temperature for 18 h, then cooled to 0° C. Methanol (6 mL) was added, and the solvents were evaporated under reduced pressure. Ethyl acetate and brine were added, and the organic extract was washed with brine, dried over sodium sulfate, filtered and evaporated to dryness. The residue was subjected to silica gel chromatography [ethyl acetate (20–25%) in hexanes] to give 6.2 g of the titled compound as a white solid.

Preparation of 2,3,5-tri-O-benzoyl-1-O-methyl-4-C-methyl-β-D-ribofuranose

A solution of benzoyl chloride (1.5 mL, 13 mmol) in pyridine (6 mL) was added to a solution of 4-C-(4,4'-dimethoxytrityloxymethyl)-2,3-O-isopropylidene-1-O-methyl-β-D-ribofuranose (6.2 g, 12 mmol) in pyridine (52 mL) stirred at 0° C. The reaction mixture was stirred at room temperature for 15 h, then cooled to 0° C. Methanol (5 mL) was added, and the solvents were evaporated under reduced pressure. Ethyl acetate and brine were added, and the organic extract was washed with brine, dried over sodium sulfate, filtered and evaporated to dryness. The residue was co-evaporated with toluene and dissolved in a solution of 80% of acetic acid in water (174 mL). The reaction mixture was stirred at room temperature for 2 hours, then the solvent was evaporated under reduced pressure. The residue was subjected to silica gel chromatography [methanol (1–2%) in dichloromethane] to remove most of the impurities, and the white foam obtained was dissolved in acetonitrile (174 mL). This solvent was stirred at 0° C. and then N,N-dimethylaminopyridine (4.3 g, 35 mmol) and phenoxythiocarbonyl chloride (2.4 mL, 17 mmol) were added. The reaction mixture was stirred at room temperature for 2 h again and the solvent was evaporated. The residue was dissolved with dichloromethane and water, and the resulting organic extract was washed with a 0.5 N solution of hydrochloric acid, then with water and finally with brine. It was dried over sodium sulfate, filtered, and the filtrate was evaporated under reduced pressure. The residue was dissolved with toluene, and tris(trimethylsilyl)silane (9.0 mL, 29 mmol) and 1,1'-azobis(cyclohexanecarbonitrile) (0.71 g, 2.9 mmol) were added. The reaction mixture was stirred at 100° C. for 15 h, then cooled to room temperature and the solvent was evaporated under reduced pressure. The residue was subjected to silica gel chromatography [methanol (1–2%) in dichloromethane] to remove most of the impurities, and the oil obtained was dissolved in a −15° C. solution of trifluoroacetic acid in water (90% v/v, 21 mL). The reaction mixture was stirred at −10° C. for 1 h, then the solvent was evaporated under high vacuum and low temperature. The residue was coevaporated with methanol and subjected to silica gel chromatography [methanol (0–3%) in dichloromethane] to remove most of the impurities. The oil obtained was dissolved with pyridine (18 mL) and the solution was stirred at 0° C. Benzoyl chloride (1.4 mL, 12 mmol) was added and the reaction mixture was stirred at room temperature for 16 h, then cooled to 0° C. Methanol was added and the solvents were evaporated under reduced pressure. Ethyl acetate, hexanes and brine were added to the residue, and the resulting organic extract was dried over sodium sulfate, filtered and the filtrate was evaporated to dryness. The residue was subjected to silica gel chromatography [ethyl acetate (25%) in hexanes] to give 1.8 g (32%, 6 steps) of the titled compound as a syrup.

Preparation of 1-O-acetyl-2,3,5-tri-O-benzoyl-4-C-methyl-β-D-ribofuranose

Concentrated sulfuric acid (97%, 99 mL) was added to a solution of 2,3,5-tri-O-benzoyl-1-O-methyl-4-C-methyl-β-D-ribofuranose (1.8 g, 3.6 mmoles) in a mixture of acetic acid (9.0 mL) and acetic anhydride (0.90 mL) at 0° C. The reaction mixture was stirred at 25° C. for 16 h and diluted with ethyl acetate (50 mL) and brine (10 mL). The organic extract was washed with brine (3 times), with a saturated aqueous solution of sodium bicarbonate, dried over sodium sulfate, filtered, and the filtrate was evaporated to dryness. The residue was dissolved with a mixture of ethyl acetate and hexanes (1:4, v/v) and the b anomer of the title compound crystallized instantaneously. The white crystals were filtered to give 1.1 g (56%) of the title compound in its pure b anomer form. The filtrate was subjected to silica gel chromatography [ethyl acetate (20%) in hexanes] to give 0.6 g (32%) of the titled compound as an oil (3:1 mixture of a/b anomers).

Preparation of 5-O-(4,4'-dimethoxytrityl-4-C-hydroxymethyl-2,3-O-isopropylidene-1-O-methyl-β-D-ribofuranose A solution of tert-butyldimethylsilyl chloride (3.4 g, 23 mmol) in pyridine (16 mL) was added to a solution of 4-C-hydroxymethyl-2,3-O-isopropylidene-1-O-methyl-β-D-ribofuranose (4.5 g, 19 mmol) in pyridine (80 mL), and stirred at 0° C. The reaction mixture was then stirred at room temperature for 24 h, then cooled to 0° C. Water (5 mL) was added, and the solvent was evaporated under reduced pressure. Ethyl acetate and brine were added, and the organic extract was washed with brine, dried over sodium sulfate, filtered and evaporated to dryness. The residue was dissolved in pyridine and the solution was stirred at 0° C. 4,4'-Dimethoxytrityl chloride (8.4 g, 25 mmol) was added, and the reaction mixture was stirred at room temperature for 16 hours, then cooled to 0° C. Methanol (10 mL) was added, and the solvents were evaporated under reduced pressure. Ethyl acetate, hexanes and brine were added, and the organic extract was washed with a 0.5 N solution of hydrochloric acid, then with brine, dried over sodium sulfate, filtered and evaporated to dryness. The residue was dissolved in tetrahydrofuran (57 mL), and a solution of tetrabutylammonium fluoride (TBAF, 1 M in tetrahydrofuran, 23 mL) was added. After 24 h at room temperature, 0.2 equivalent of TBAF was added, and the mixture was stirred for an additional 36 h. The solvent was evaporated and the residue was subjected to silica gel chromatography [ethyl acetate (50%) in hexanes] to give 6.6 g (65%, 3 steps) of the titled compound as a white solid.

Preparation of 5-O-(4,4'-dimethoxytrityl)-2,3-O-isopropylidene-1-O-methyl-4-C-vinyl-β-D-ribofuranose A solution of trifluoroacetic acid (0.49 mL, 6.4 mmol) and pyridine (1.6 mL, 19 mmol) in dimethylsulfoxide (11 mL) was added to a solution of 5-O-(4,4'-dimethoxytrityl)-4-C-hydroxymethyl-2,3-O-isopropylidene-1-O-methyl-β-D-ribofuranose (6.9 g, 13 mmol) and N,N'-dicyclohexylcarbodiimide (6.6 g, 32 mmol) in a mixture of toluene (26 mL) and dimethylsulfoxide (66 mL) stirred at 5° C. The reaction mixture was then stirred at room temperature for 8 h, then cooled to 0° C. Ethyl acetate (80 mL) and a solution of oxalic acid (1.8 g, 19 mmol) in methanol (10 mL) were added, and the mixture was stirred at room temperature for 15 h. The precipitate was filtered and washed with a 1:1 mixture of hexanes and ethyl acetate. The filtrate was washed with brine, with a saturated aqueous solution of sodium bicarbonate, washed with brine again, dried over sodium sulfate, filtered, and the filtrate was evaporated to dryness. The residue was subjected to silica gel chromatography [ethyl acetate (25%) in hexanes] to give 6.1 g (89%) of 5-O-(4,4'-dimethoxytrityl)-4-C-formyl-2,3-O-isopropylidene-1-O-methyl-β-D-ribofuranose as a white solid.

A solution of sodium pentoxide (2.5 g, 22 mmol) in benzene (34 mL) was added to a suspension of methylphosphonium bromide (8.8 g, 25 mmol) in ether stirred at room temperature. The mixture was stirred at room temperature for 6 h, and a solution of 5-O-(4,4'-dimethoxytrityl)-4-C-formyl-2,3-O-isopropylidene-1-O-methyl-β-D-ribofuranose (6.0 g, 11 mmol) in ether (30 mL) was added. The resulting mixture was stirred at room temperature for 18 h, then cooled to 0° C. Brine (100 mL) was added, followed by ethyl acetate (300 mL). The organic extract was washed with brine, dried over sodium sulfate, filtered and the filtrate was evaporated to dryness. The residue was subjected to silica gel chromatography [ethyl acetate (25%) in hexanes] to give 5.9 g (99%) of the titled compound as a white solid.

Preparation of 5-O-benzoyl-4-C-ethyl-1-O-methyl-b-D-ribofuranose

Palladium on activated carbon (10% Pd, 50% water, 508 mg) was added to a solution of 5-O-(4,4'-dimethoxytrityl)-2,3-O-isopropylidene-1-O-methyl-4-C-vinyl-β-D-ribofuranose (5.0 g, 9.4 mmol) in methanol (254 mL). The flask was shaken under 5 psi of hydrogen during 6 h and the catalyst was filtered and washed with methanol. The solvent was evaporated, and the residue was coevaporated with pyridine. It was then dissolved in pyridine (75 mL) and stirred at 0° C. Benzoyl chloride (1.2 mL, 10 mmol) was added, the reaction mixture was stirred at room temperature for 15 h, then cooled to 0° C. Methanol (5 mL) was added, and the solvents were evaporated under reduced pressure. Ethyl acetate, Hexane and brine were added, and the organic extract was washed with brine, dried over sodium sulfate, filtered and evaporated to dryness. The residue was coevaporated with toluene and dissolved in a −15° C. solution of trifluoroacetic acid in water (90% v/v, 57 mL). The reaction mixture was stirred at −10° C. for 2 h, then the solvent was evaporated under high vacuum and low temperature. The residue was coevaporated with methanol, and a white precipitate was formed. It was removed by filtration, and the filtrate containing the titled compound was evaporated to dryness, and dissolved in ethyl acetate, hexane and brine. The organic extract was washed with a saturated aqueous solution of sodium bicarbonate, washed with brine, dried over sodium sulfate, filtered, and the filtrate was evaporated to dryness. The residue was subjected to silica gel chromatography [ethyl acetate (33%) in hexanes] to give 1.8 g (63%, 3 steps) of the titled compound as an oil.

Preparation of 1-O-acetyl-2,3,5-tri-O-benzoyl-4-C-ethyl-β-D-ribofuranose

Benzoyl chloride (1.5 mL, 13 mmol) was added to a solution of 5-O-benzoyl-4-C-ethyl-1-O-methyl-b-D-ribofuranose in pyridine (41 mL) stirred at 0° C., and the reaction mixture was stirred at room temperature for 18 h, then cooled to 0° C. Methanol (5 mL) was added, and the solvents were evaporated under reduced pressure. Ethyl acetate, Hexane and brine were added, and the organic extract was washed with a 0.5 N solution of hydrochloric acid, then with brine, dried over sodium sulfate, filtered and evaporated to dryness. The residue was coevaporated with toluene and dissolved in a mixture of acetic acid (14 mL) and acetic anhydride (1.5 mL). Sulfuric acid (97%, 165 mL) diluted in acetic acid (1 mL) was added at 5° C. The reaction mixture was stirred at 25° C. for 4 h and diluted with ethyl acetate (50 mL) and brine (10 mL). The organic extract was washed with brine (3 times), with a saturated aqueous solution of sodium bicarbonate, washed with brine, dried over sodium sulfate, filtered, and the filtrate was evaporated to dryness. The residue was subjected to silica gel chromatography [ethyl acetate (0–3%) in dichloromethane] to give 2.9 g (92%) of the titled compound as an oil (2:1 mixture of b/a anomers).

Preparation of 4-amino-5-oxo-pyrido[2,3-d]pyrimidine

Trimethylsilyl chloride (7.6 mL, 60 mmoles) was added to a stirred suspension of 2-amino-3-cyano-4-methoxy-pyridine (*Archiv der Pharmazie* 1985, 318, 481–486; 7.5 g, 50 mmoles) and sodium iodide (7.50 g, 50 mmoles) in acetonitrile (225 mL). The resulting mixture was heated at reflux temperature for 24 h. The precipitate was filtered and washed with ethyl acetate to give 10.4 g of a brownish powder (2-amino-3-cyano-4-oxo-pyridine). This powder was dried under reduced pressure, and suspended in 2-ethoxyethanol (300 mL). Formamidine acetate (31.2 g, 300 mmoles) was added, and the suspension was heated at reflux temperature for 2 days, and then filtered. The grey residue obtained was dissolved in a 2:1 boiling mixture of acetic acid and water, and charcoal was added. The black suspension was filtered, and the filtrate was evaporated to dryness to give a white solid, which was suspended in a hot saturated solution of sodium hydrogencarbonate in water. The suspension was filtered to give 4-amino-5-oxo-pyrido[2,3-d]pyrimidine (2.0 g) as a white solid.

Preparation of 4-amino-5-oxo-8-(2,3,5-tri-O-benzoyl-4-C-methyl-β-D-ribofuranosyl)pyrido[2,3-d]pyrimidine 4-Amino-5-oxo-pyrido[2,3-d]pyrimidine (0.23 g, 1.4 mmoles) was suspended in 1,2-dichloroethane (20 mL) and the mixture was stirred at 55° C. BSA (0.87 mL, 3.5 mmoles) was added, the reaction mixture was stirred at reflux temperature for 90 min, then cooled to 40° C. 1-O-acetyl-2,3,5-tri-O-benzoyl-4-C-methyl-b-D-ribofuranose (0.60 g, 1.2 mmoles) in 1,2-dichloroethane (3 mL) and TMSOTf (0.42 mL, 2.3 mmoles) were added to the clear solution, and the mixture was stirred at 100° C. for 48 h. The mixture was cooled to room temperature and a saturated solution of sodium hydrogencarbonate in water was added. The mixture was diluted with ethyl acetate (100 mL) and the organic extract was washed with brine, dried over sodium sulfate, filtered, and the filtrate was evaporated to dryness. The residue was subjected to silica gel chromatography [acetone (15–25%) in dichloromethane] to give 0.30 g (41%) of the titled compound as a white solid, and 0.14 g (19%) of 4-amino-5-oxo-1-(2,3,5-tri-O-benzoyl-4-C-methyl-b-D-ribofuranosyl)pyrido[2,3-d]pyrimidine as a white solid. Similarly, the following compounds were prepared: 4-Amino-5-oxo-8-(2,3,5-tri-O-benzoyl-4-C-benzoyloxymethyl-β-D-ribofuranosyl)pyrido-[2,3-d]pyrimidine as a white solid from 4-amino-5-oxo-pyrido[2,3-d]pyrimidine and 1-O-acetyl-2,3,5-tri-O-benzoyl-4-C-benzoyloxymethyl-β-D-ribofuranose; 4-Amino-5-oxo-8-(2,3,5-tri-O-benzoyl-5(R,S)-C-ethynyl-β-D-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-5(R,S)-C-ethynyl-β-D-ribofuranose; 4-Amino-5-oxo-8-(2,3,5-tri-O-benzoyl-β-L-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-β-L-ribofuranose; 4-Amino-5-oxo-8-(2,3,5-tri-O-benzoyl-β-D-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-β-D-ribofuranose; 4-Amino-5-oxo-8-(2,3,5-tri-O-benzoyl-5(R)-C-allyl-β-D-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-5(R)-C-allyl-β-D-ribofuranose; 4-Amino-5-oxo-8-(2,3,5-tri-O-benzoyl-5(R)-C-methyl-β-D-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-5(R)-C-methyl-β-D-ribofuranose; 4-Amino-5-oxo-8-(2,3,5-tri-O-benzoyl-4-C-ethyl-β-D-ribofuranosyl)pyrido[2,3-d]

pyrimidine as a white solid from 4-amino-5-oxo-pyrido[2,3-d]pyrimidine and 1-O-acetyl-2,3,5-tri-O-benzoyl-4-C-ethyl-β-D-ribofuranose; 4-Amino-5-oxo-8-(2,3,5-tri-O-benzoyl-5(R,S)-C-vinyl-β-D-ribofuranosyl)pyrido[2,3-d]pyrimidine as a white solid from 4-amino-5-oxo-pyrido[2,3-d]pyrimidine and 1-O-acetyl-2,3,5-tri-O-benzoyl-5(R,S)-C-vinyl-β-D-ribofuranose.

Preparation of 4-amino-5-oxo-8-(4-C-hydroxymethyl-β-D-ribofuranosyl)pyrido-[2,3d]pyrimidine A solution of 4-amino-5-oxo-8-(2,3,5-tri-O-benzoyl-4-C-benzoyloxymethyl-β-D-ribofuranosyl)pyrido[2,3-d]pyrimidine (0.82 g, 1.1 mmole) in methanolic ammonia (saturated at 0° C.) was stirred in a sealed flask at 25° C. for 15 h. The solvents were evaporated, and the residue was subjected to silica gel chromatography [methanol (30%) in dichloromethane] to give 0.36 g of the titled compound as a white solid. Similarly, the following compounds were prepared: 4-Amino-5-oxo-8-(5(R)-C-methyl-β-D-ribofuranosyl)pyrido[2,3-d]pyrimidine from 4-amino-5-oxo-8-(2,3,5-tri-O-benzoyl-5(R)-C-methyl-β-D-ribofuranosyl)pyrido[2,3-d]pyrimidine; 4-Amino-5-oxo-8-(5(R)-C-allyl-β-D-ribofuranosyl)pyrido[2,3-d]pyrimidine from 4-amino-5-oxo-8-(2,3,5-tri-O-benzoyl-5(R)-C-allyl-β-D-ribofuranosyl)pyrido[2,3-d]pyrimidine; 4-Amino-5-oxo-8-(5(R,S)-C-ethynyl-β-D-ribofuranosyl)pyrido[2,3-d]pyrimidine from 4-amino-5-oxo-8-(2,3,5-tri-O-benzoyl-5(R,S)-C-ethynyl-β-D-ribofuranosyl)pyrido[2,3-d]pyrimidine; 4-Amino-5-oxo-8-(5(R,S)-C-vinyl-β-D-ribofuranosyl)pyrido[2,3-d]pyrimidine from 4-amino-5-oxo-8-(2,3,5-tri-O-benzoyl-5(R,S)-C-vinyl-β-D-ribofuranosyl)pyrido[2,3-d]pyrimidine; 4-Amino-5-oxo-8-(β-D-ribofuranosyl)pyrido[2,3-d]pyrimidine from 4-amino-5-oxo-8-(2,3,5-tri-O-benzoyl-β-D-ribofuranosyl)pyrido[2,3-d]pyrimidine; 4-Amino-5-oxo-8-(β-L-ribofuranosyl)pyrido[2,3-d]pyrimidine from 4-amino-5-oxo-8-(2,3,5-tri-O-benzoyl-β-L-ribofuranosyl)pyrido[2,3-d]pyrimidine; 4-Amino-5-oxo-8-(4-C-methyl-β-D-ribofuranosyl)pyrido[2,3-d]pyrimidine from 4-amino-5-oxo-8-(2,3,5-tri-O-benzoyl-4-C-methyl-β-D-ribofuranosyl)pyrido[2,3-d]pyrimidine; 4-Amino-5-oxo-8-(4-C-ethyl-β-D-ribofuranosyl)pyrido[2,3-d]pyrimidine from 4-amino-5-oxo-8-(2,3,5-tri-O-benzoyl-4-C-ethyl-β-D-ribofuranosyl)pyrido[2,3-d]pyrimidine.

Preparation of 4-amino-5-oxo-8-(5(R,S)-C-ethyl-β-D-ribofuranosyl)pyrido-[2,3d]pyrimidine Palladium on activated carbon (10% Pd, 200 mg) was added to a solution of 4-amino-5-oxo-8-(5-C-ethynyl-b-D-ribofuranosyl)pyrido[2,3-d]pyrimidine (0.14 g, 0.45 mmole) in methanol (50 mL). The flask was shaken under 3 psi of hydrogen during 2 h and the catalyst was filtered and washed with methanol. The solvents were evaporated, and the residue was subjected to silica gel chromatography [methanol (10%) in dichloromethane] to give 0.12 g of the titled compound as a white solid. Similarly, the following compounds were prepared: 4-Amino-5-oxo-8-(5(R)-C-propyl-β-D-ribofuranosyl) pyrido[2,3-d]pyrimidine from 4-amino-5-oxo-8-(5(R)-C-allyl-β-D-ribofuranosyl)pyrido[2,3-d]pyrimidine.

Preparation of 4-amino-5-oxo-8-(2-deoxy-β-D-ribofuranosyl)pyrido[2,3-d]pyrimidine A reaction mixture of 4-amino-5-oxo-8-(β-D-ribofuranosyl)pyrido[2,3-d]pyrimidine (1.8 g, 6.20 mmol) and 1,3-dichloro-1,1,3,3-tetraisopropyldisiloxane (2.15 mL, 6.73 mmol) in anhydrous pyridine (25 mL) was stirred at room temperature for 20 h and cooled with ice. Water (0.5 mL) was added, and the mixture stirred at ambient temperature for 30 min and concentrated. The residue was dissolved in ethyl acetate, washed with diluted sodium bicarbonate, dried over $Na_2SO_4$, and concentrated. Chromatography on silica (EtOAc-hexanes 3:2) gave 2.0 g of 4-amino-5-oxo-8-[3,5-O-(1,1,3,3-tetraisopropyldisiloxy)-β-D-ribofuranosyl)]pyrido[2,3-d]pyrimidine.

To a solution of 4-amino-5-oxo-8-[3,5-O-(1,1,3,3-tetraisopropyldisiloxy)-β-D-ribofuranosyl)]pyrido[2,3-d]pyrimidine (650 mg, 1.21 mmol) and DMAP (295 mg, 2.42 mmol) in acetonitrile (10 mL) was added phenyl chlorothioformate (185 mL, 1.33 mmol). The mixture was stirred at room temperature for 2 h and concentrated to dryness. The residue was dissolved in chloroform, washed with water, dried ($Na_2SO_4$), and concentrated. The residue was dried under vacuum for 30 min and then dissolved in toluene (10 ML). 1,1'-Azobis(cyclohexanecarbonitrile) (74 mg, 0.30 mmol) was added and the resulting solution was bubbled with argon for 30 min. Tris(trimethylsilyl)silane (0.56 mL, 1.82 mmol) was added and the resulting mixture stirred at 80° C. for 2 h and then at 105° C. overnight. Solvent was evaporated and residue dissolved in THF (5 mL). TBAF (1.0 M in THF, 2.5 mL) was added and the resulting solution stood at room temperature for 2 h and concentrated. Chromatography on silica (10% MeOH in $CH_2Cl_2$) gave 240 mg of the titled compound.

In Vitro/In Vivo Experiments

Unless indicated otherwise, the following experiments were conducted with 4-amino-5-oxo-8-(β-D-ribofuranosyl)pyrido[2,3-d]pyrimidine.

Determination of $EC_{50}$

Cancer cells were incubated with 4-amino-5-oxo-8-(β-D-ribofuranosyl)pyrido[2,3-d]pyrimidine at various concentrations for a period of at least 24 hours and $EC_{50}$ was determined. Table 1 gives in vitro activity of 4-amino-5-oxo-8-(β-D-ribofuranosyl)pyrido[2,3-d]pyrimidine in nM concentrations.

| Tumor Type | Cell lines | $EC_{50}$ [nM] |
| --- | --- | --- |
| Breast | MCF 7, NCI/ADR-RES, MDA-MB-435, BT-549, T-47D | 18 |
| Prostate | PC-3, DU-145 | 19 |
| Kidney | 786-0, A498, ACHN, CAKI-1, RXF 393, UO-31 | 44 |
| Ovarian | IGROV1, OVCAR-3, OVCAR-4, OVCAR-5, SK-OV-3 | 21 |
| Melanoma | LOX IM VI, MALME-3M, M14, SK-MEL-2, SK-MEL-28, ACC-257, UACC-62 | 30 |
| CNS | SF-268, SF-295, SF-539, SNB-19, SNB-75, U251 | 125 |
| Colon | SW-620, KM 12, HT29, HCT-15, CHCT-116, HCC-2998, COLO-205 | 16 |
| Lung | NCI-H522, NCI-H460, NCI-H322M, NCI-H23, HOP-92, HOP-62, EKVX, A549 | 68 |
| Leukemia | SR, RPMI 8226, MOLT-4, K-562, HL-60, CCRF-CEM | 34 |
| Liver | PLC/PRF5, Hep3B, Huh7 | 288 |
| Pancreas | PaCa-2, PANC-1 | 188 |

Figure 2:
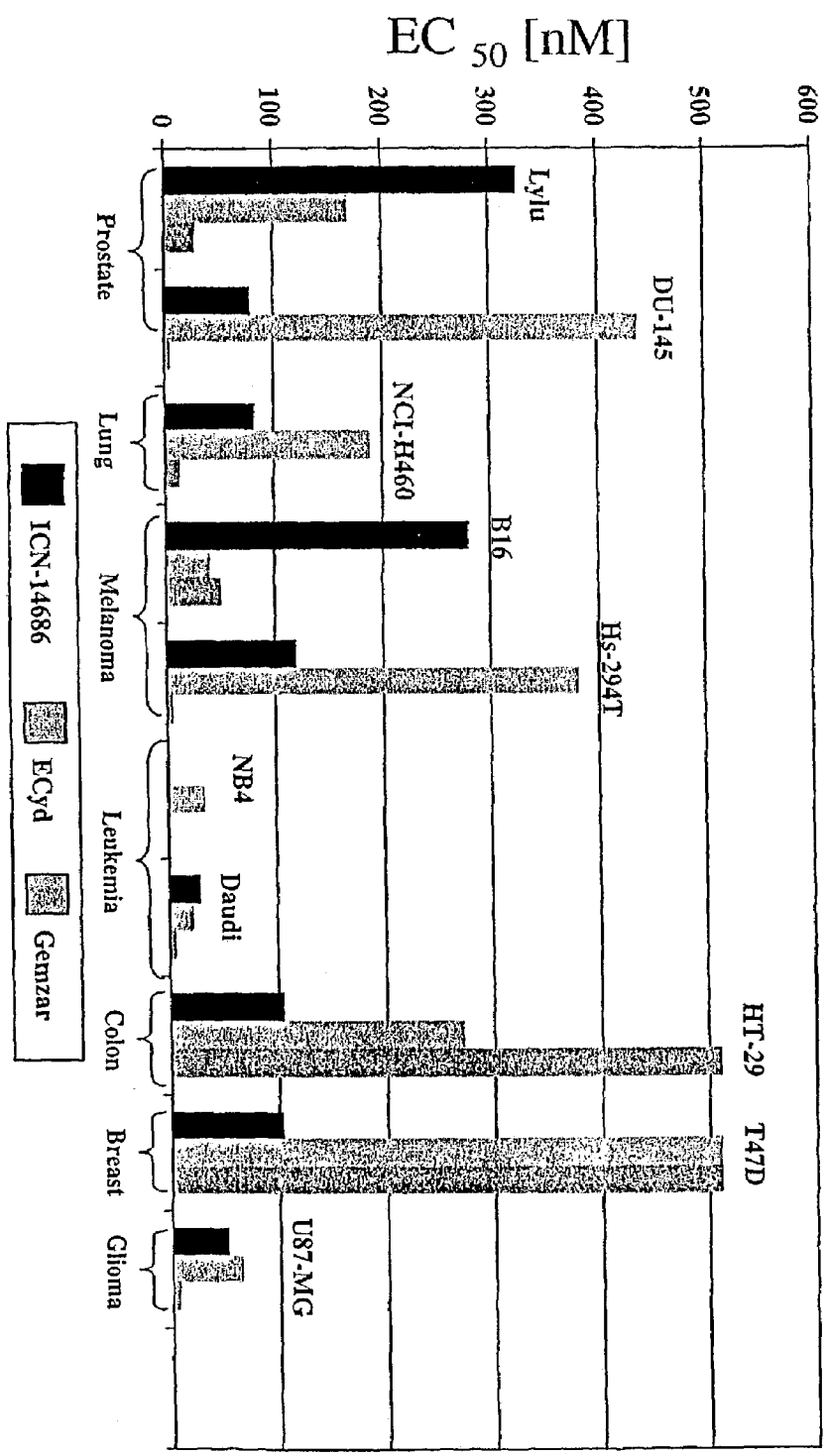
FIG. 2 is a graph depicting comparative inhibition of proliferation of various cancer cells by exemplary contemplated compounds.

The relatively high efficacy of contemplated compounds, and especially of 4-amino-5-oxo-8-(β-D-ribofuranosyl)pyrido[2,3-d]pyrimidine is further reflected in a series of experiments in which cytotoxicity and inhibition of proliferation of various cancer cell lines were compared with commercially available cytostatic agents. The results of the experiments are shown in FIGS. 1 and 2.

Anti-Clonogenic Activity of Contemplated Compounds

Figure 3:
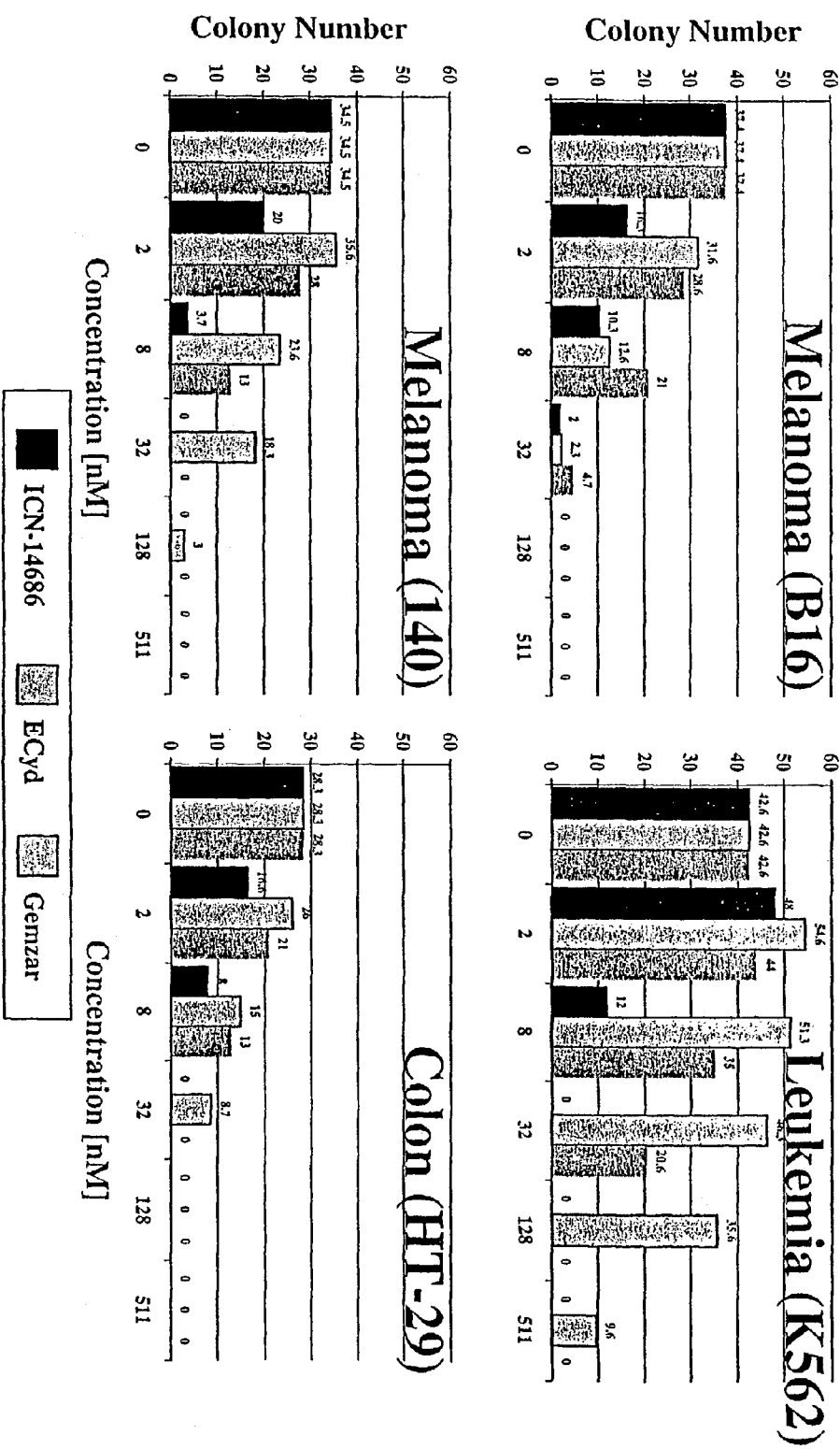
FIG. 3 is a graph depicting comparative anti-clonogenic activity of exemplary contemplated compounds in various cancer cells.

To determine the anti-clonogenic activity of contemplated compounds in various cancer cells experiments were conducted. The results of these experiments is shown in FIG. 3, clearly indicating that contemplated compounds exhibit significant anti-clonogenic activity, especially in melanoma B16 and 140 cells, Leukemia cells (K562, M), and colon HT-29 cells. Here again, 4-amino-5-oxo-8-(β-D-ribofuranosyl)pyrido[2,3-d]pyrimidine was used as a representative compound of contemplated compounds and compared against Ecyd and Gemzar.

Induction of Apoptosis

Figure 4A:
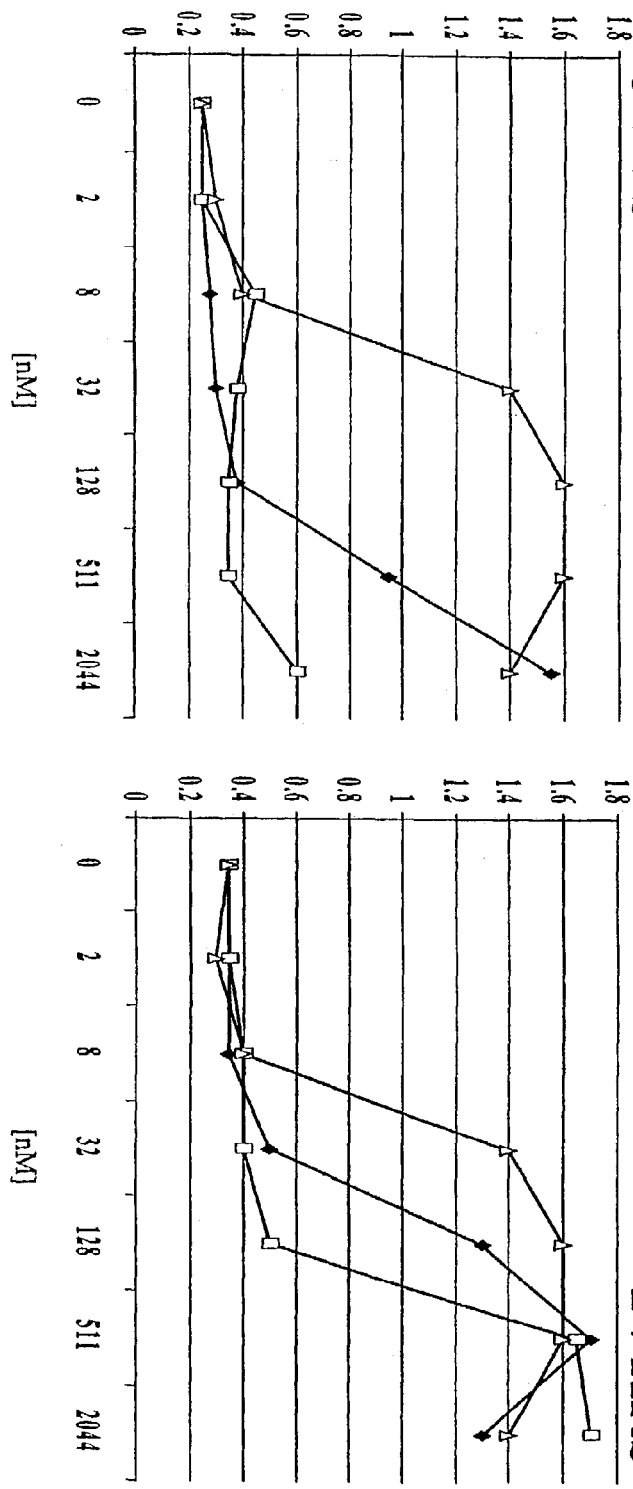
FIGS. 4A and 4B are graphs depicting induction of apoptosis in various cancer cells by exemplary contemplated compounds.
Figure 4B:
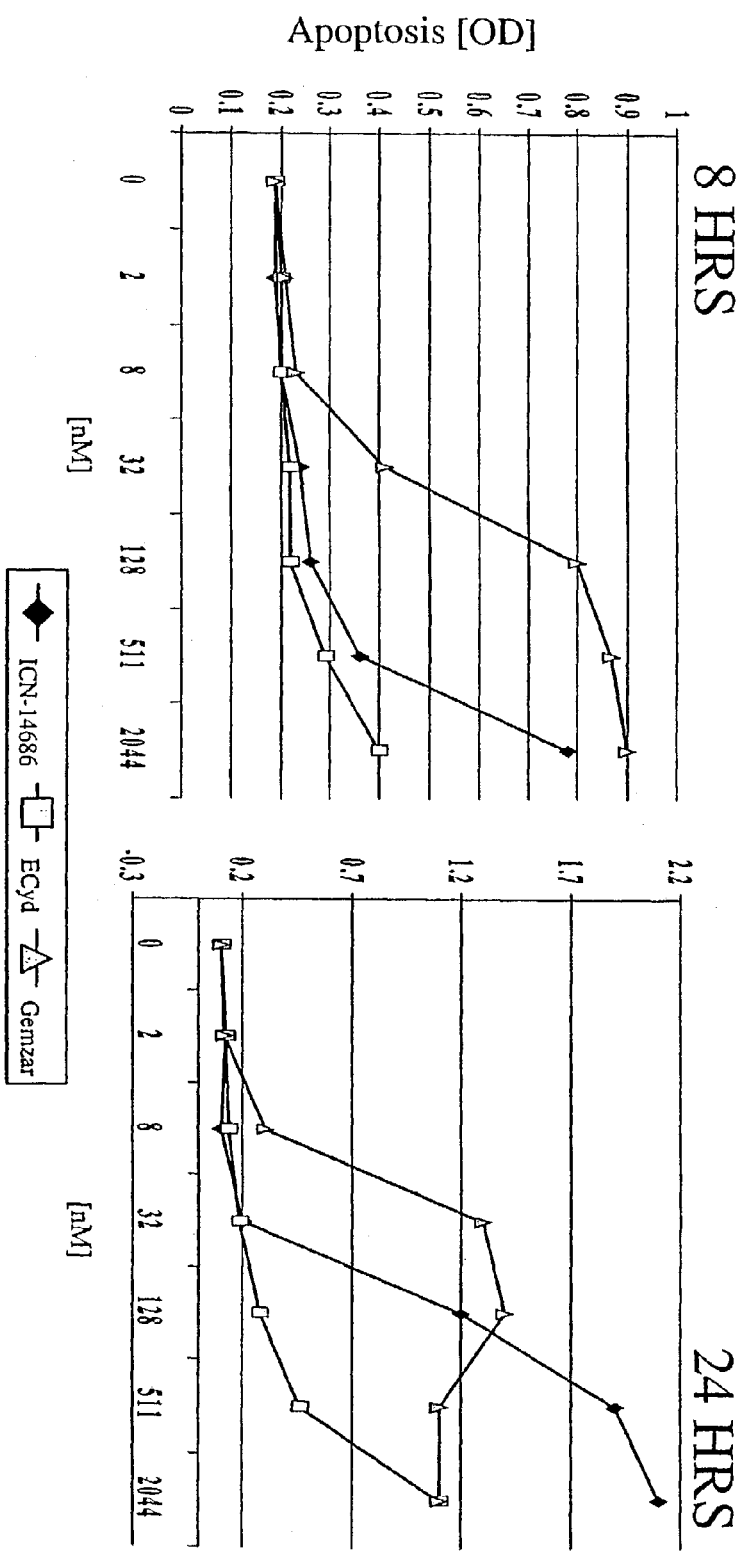

In order to determine how contemplated compounds interact with cancer cells, NB4 cells (Leukemia) and Prostate 81 (prostate cancer cells) cells were incubated with 4-amino-5-oxo-8-(β-D-ribofuranosyl)pyrido[2,3-d]pyrimidine, Ecyd, and Gemzar, and apoptosis was monitored by histone-DNA ELISA. The results are shown in FIGS. 4A and 4B and suggest that contemplated compounds induce apoptosis in a dose dependent manner.

Inhibition of RNA Synthesis

Figure 5:
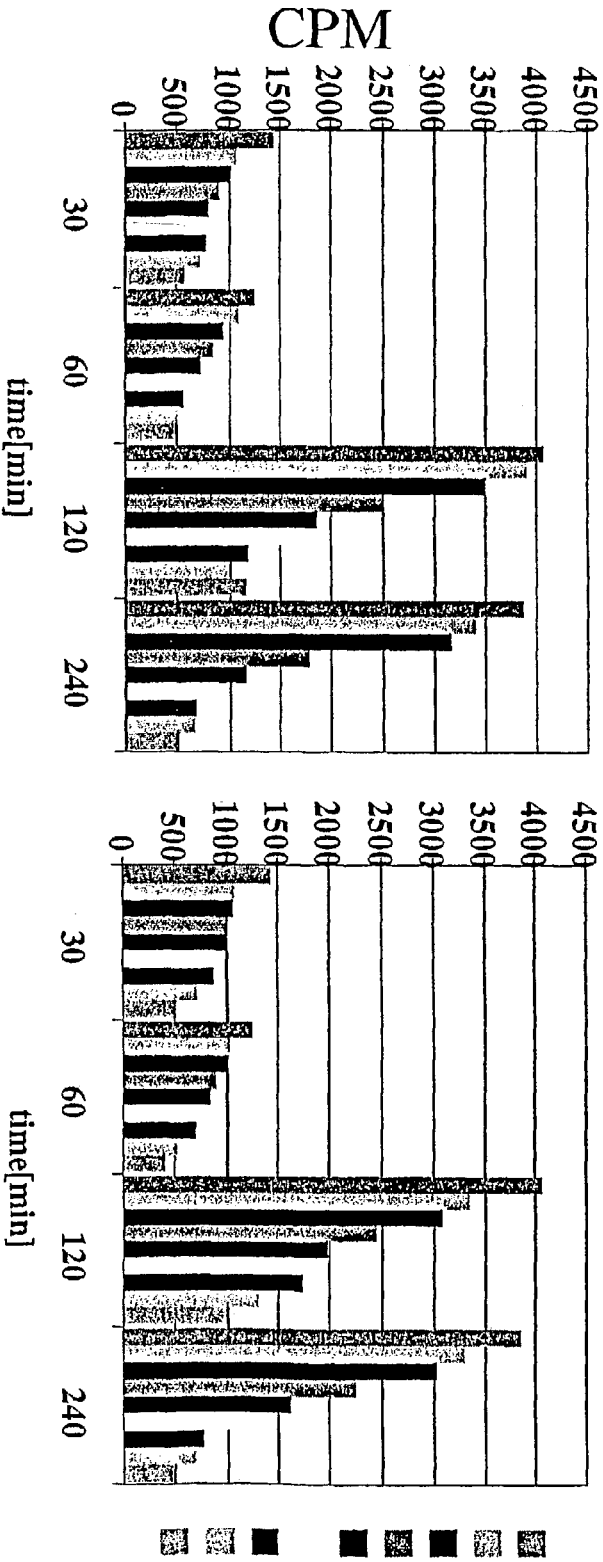
FIG. 5 is a graph depicting inhibition of RNA synthesis in K562 cells by exemplary contemplated compounds.

RNA synthesis was monitored in K562 cells using $H^3$-Uridine incorporation following a general protocol as outlined below. FIG. 5 shows inhibition of RNA synthesis by exemplary contemplated compounds (here represented by 4-amino-5-oxo-8-(β-D-ribofuranosyl)pyrido[2,3-d]pyrimidine) over various time periods and concentrations.

Inhibition of RNA Polymerase I, II, and III

Figure 6:
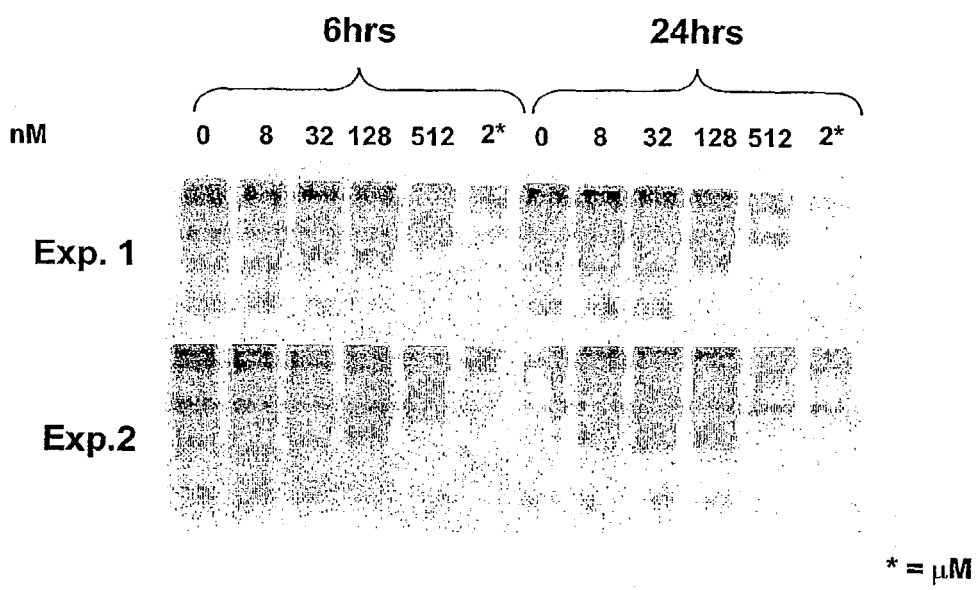
FIG. 6 is a graph depicting inhibition of RNA Polymerase I & III by exemplary contemplated compounds.
Figure 7:
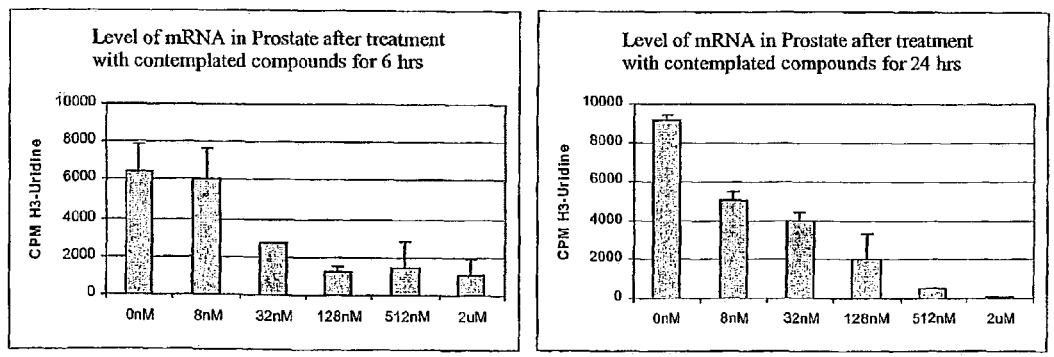
FIG. 7 is a graph depicting inhibition of RNA Polymerase II by exemplary contemplated compounds.

To further investigate the influence of contemplated compounds (here again represented by 4-amino-5-oxo-8-(β-D-ribofuranosyl)pyrido[2,3-d]pyrimidine) on RNA synthesis dependent on RNA Polymerase I, II, and III, experiments were conducted. The results of these experiments are shown in FIGS. 6 and 7 and suggest that contemplated compounds may inhibit processing of 28S and 18S rRNA, however, fail to significantly inhibit RNA Polymerase III. The experiments further indicate that contemplated compounds inhibit RNA-Polymerase II dependent RNA synthesis in a concentration dependent manner.

MEK-ERK Phosphorylation

Figure 8:
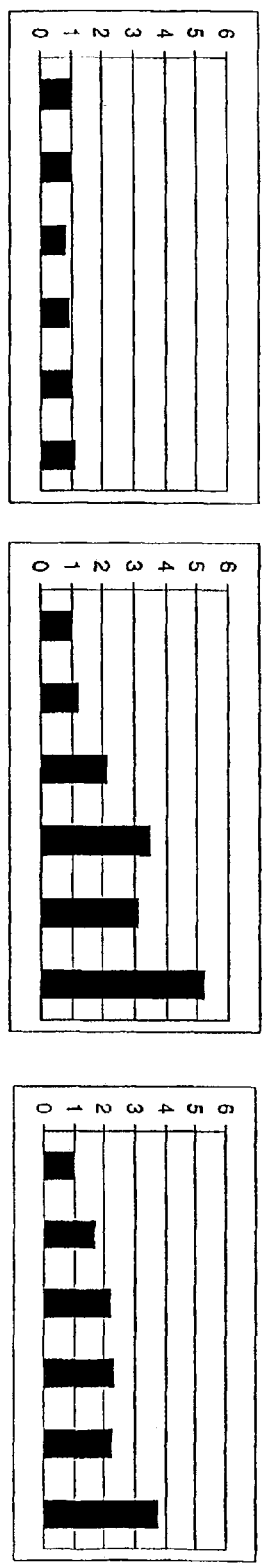
FIG. 8 is an autoradiograph depicting MEK-ERK phosphorylation by exemplary contemplated compounds.
Figure 8:

It has recently been demonstrated [Wang, et al. JBC 275:39435–43 (2000); Pavlovic et al., Eur. Cytokine Netw 2:267–74 (2000)] that apoptosis can be induced via the MEK-ERK signal transduction pathway. To investigate the possibility of activation of the MEK-ERK signal transduction pathway by contemplated compounds an experiment was conducted. FIG. 8 is an autoradiograph depicting phosphorylation of MEK and ERK, but not Raf by contemplated compounds (represented by 4-amino-5-oxo-8-(β-D-ribofuranosyl)pyrido[2,3-d]pyrimidine) in NB4 leukemic cells. This, and other experiments suggest that the contemplated compounds enhance phosphorylation of MEK (which is in contrast to Ecyd and Gemzar), however, they do not enhance phosphorylation of Raf. Consequently, it is contemplated that the compounds according to the inventive subject matter may induce apoptosis through activation of MEK (which can be abolished by inhibitors of the MEK-ERK pathway).

Metabolites of Contemplated Compounds

Numerous experiments (data not shown) suggest that contemplated compounds are phosphorylated within a (tumor) cell, and that the products include mono-, di-, and triphosphorylated forms (e.g., detectable by LC-MS). It is further contemplated that the metabolites may have significant (or even increased) biological activity.

Thus, specific embodiments and applications of pyrido[2,3-d]pyrimidine and pyrimido[4,5-d]pyrimidine nucleosides have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A nucleoside analog according to the formula (I)

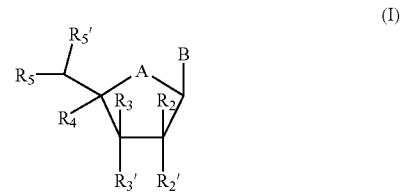

(I)

wherein

A is O;

$R_2$, $R_2'$, $R_3$, and $R_3'$ are independently selected from H, F, OH, $NH_2$, CN, $N_3$, $CONH_2$, and R, where R is lower alkyl, lower alkenyl, lower alkynyl, or lower acyl;

or $R_2$ and $R_2'$ together, or $R_3$ and $R_3'$ together are selected from =$CH_2$, =CHR", =CR"$_2$, =NR", where R" is H, F, OH, CN, $N_3$, $CONH_2$, lower alkyl, lower alkenyl, lower alkynyl, or lower acyl;

$R_4$ is selected from H, lower alkyl, lower alkenyl, lower alkynyl, aralkyl, or hydroxymethyl; $R_5'$ is selected from H, lower alkyl, lower alkenyl, lower alkynyl, or aralkyl;

$R_5$ is H, OH, OP(O)(OH)$_2$, or P(O)(OH)$_2$; and

B is selected from the group of heterocyclic radicals consisting of formulae (II) and (IV)

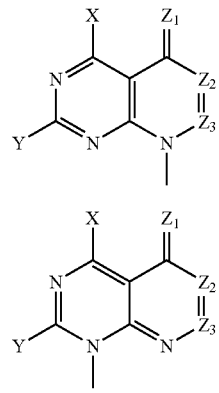

wherein X is H, NH₂ or OH;
Y is H, NH₂, or halogen;
$Z_1$ is O, S, NR", CHM, or CM₂;
$Z_3$ is N, CH, or CM;
$Z_2$ is N, CH, or CM;
where M is F, Cl, Br, OH, SH, NH₂, CN, COOR", C(=NH)NH₂, lower alkyl, lower alkenyl, lower alkynyl, aralkyl, or aryl.

2. The nucleoside analog of claim 1 wherein A is O, and B is a heterocyclic radical according to formula (II).

3. The nucleoside analog of claim 2 wherein X is NH₂, $Z_1$ is O, and $Z_2$ and $Z_3$ are CH.

4. The nucleoside analog of claim 3 wherein $R_4$ and $R_5'$ are hydrogen, and $R_5$ is OH.

5. The nucleoside analog of claim 1 having a structure according to formula (VI)

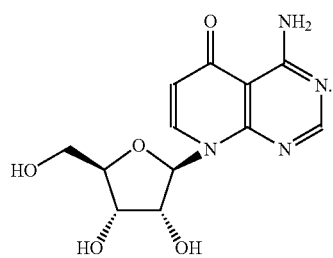

6. A prodrug comprising the nucleoside analog of claim 5.

7. The prodrug of claim 6 wherein the prodrug comprises a phosphate or phosphonate covalently coupled to the $C_5$ atom of the ribose.

8. The prodrug of claim 6 wherein the prodrug comprises a moiety that is covalently bound to at least one of the hydroxyl groups of the ribose, and that is cleaved from the at least one hydroxyl groups within a target cell.

9. The prodrug of claim 6 wherein the prodrug comprises a moiety that is covalently bound to the amino group of the base, and that is cleaved from the amino group within a target cell.

10. A method of inhibiting growth of a neoplastic cell comprising:
providing a compound according to claim 1; and
presenting the compound to the cell in a dosage effective to inhibit the growth of a cell.

11. The method of claim 10 wherein A is O, and B is a heterocyclic radical according to formula (II).

12. The method of claim 11 wherein X is NH₂, $Z_1$ is O, and $Z_2$ and $Z_3$ are CH.

13. The method of claim 12 wherein $R_4$ and $R_5'$ are hydrogen, and $R_5$ is OH.

14. The method of claim 10 wherein the compound has a structure according to formula (VI)

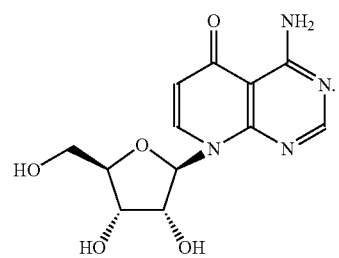

15. The method of claim 14 wherein the compound comprises a phosphate or phosphonate covalently coupled to the $C_5$ atom of the ribose.

16. The method of claim 14 wherein the compound comprises a moiety that is covalently bound to at least one of the hydroxyl groups of the ribose, and that is cleaved from the at least one hydroxyl groups within a target cell.

17. The method of claim 14 wherein the compound comprises a moiety that is covalently bound to the amino group of the base, and that is cleaved from the amino group within a target cell.

18. The use of claim 14 wherein the neoplastic cell is a cell selected from the group consisting of a colon cancer cell, a breast cancer cell, a melanoma cell, a glioma cell, prostate cancer cell, a lung cancer cell, a liver cancer cell, a pancreas cancer cell, and an ovarian cancer cell.

19. The method of claim 14 wherein the inhibition of the growth of the cell comprises apoptosis.

20. The method of claim 19 wherein the apoptosis is triggered at least in part by MEK-phosphorylation.

21. The method of claim 14 wherein the inhibition of the growth of the cell comprises inhibition of at least one of RNA polymerase I, RNA polymerase II, and RNA polymerase III.

* * * * *